US011234609B2

(12) United States Patent
Zhu et al.

(10) Patent No.: US 11,234,609 B2
(45) Date of Patent: Feb. 1, 2022

(54) TECHNIQUES FOR DETERMINING FLUID VOLUMES USING BIOIMPEDANCE INFORMATION

(71) Applicant: Fresenius Medical Care Holdings, Inc., Waltham, MA (US)

(72) Inventors: Fansan Zhu, Flushing, NY (US); Peter Kotanko, New York, NY (US); Nathan W. Levin, New York, NY (US)

(73) Assignee: Fresenius Medical Care Holdings, Inc., Watham, MA (US)

( * ) Notice: Subject to any disclaimer, the term of this patent is extended or adjusted under 35 U.S.C. 154(b) by 573 days.

(21) Appl. No.: 16/031,763

(22) Filed: Jul. 10, 2018

(65) Prior Publication Data

US 2019/0015013 A1    Jan. 17, 2019

Related U.S. Application Data

(60) Provisional application No. 62/531,254, filed on Jul. 11, 2017.

(51) Int. Cl.
*A61B 5/0537* (2021.01)
*A61B 5/053* (2021.01)
(Continued)

(52) U.S. Cl.
CPC .......... *A61B 5/0537* (2013.01); *A61B 5/0295* (2013.01); *A61B 5/02233* (2013.01);
(Continued)

(58) Field of Classification Search
CPC ..... A61B 5/0537; A61B 5/053; A61B 5/1451; A61B 5/4881; A61B 5/6828; A61B 5/0295
See application file for complete search history.

(56) References Cited

U.S. PATENT DOCUMENTS

| 2002/0188206 A1* | 12/2002 | Davis | A61B 5/0053 |
| | | | 600/485 |
| 2008/0001735 A1* | 1/2008 | Tran | G16H 80/00 |
| | | | 340/539.22 |

(Continued)

FOREIGN PATENT DOCUMENTS

| WO | 9632883 A1 | 10/1996 |
| WO | 0213691 A1 | 2/2002 |

(Continued)

OTHER PUBLICATIONS

S. Thijssen, F. Kappel and P. Kotanko, "Absolute Blood Volume in Hemodialysis Patients: Why Is It Relevant, and How to Measure It?," Blood Purification, vol. 35, pp. 63-71, 2013.

(Continued)

*Primary Examiner* — Puya Agahi
(74) *Attorney, Agent, or Firm* — Kacvinsky Daisak Bluni PLLC

(57) ABSTRACT

Techniques and apparatuses for determining fluid volumes of a patient are described. In one embodiment, for example, an apparatus may include at least one memory, and logic coupled to the at least one memory. The logic may be configured to receive baseline bioimpedance information for at least a portion of a human body at a baseline pressure, receive pressurized bioimpedance information of the portion of the human body at a pressurized pressure, the pressurized pressure greater than the baseline pressure and configured to substantially remove blood volume from the portion at the pressurized pressure, and determine at least one of interstitial fluid volume ($V_{IT}$) or peripheral blood volume ($BV_P$) based on the baseline bioimpedance information and the pressurized bioimpedance information. Other embodiments are described.

20 Claims, 13 Drawing Sheets

(51) Int. Cl.
- *A61B 5/145* (2006.01)
- *A61B 5/00* (2006.01)
- *G16H 50/20* (2018.01)
- *A61B 5/022* (2006.01)
- *A61B 5/0295* (2006.01)
- *A61M 1/28* (2006.01)
- *G06F 17/18* (2006.01)
- *A61B 5/02* (2006.01)

(52) U.S. Cl.
CPC .......... *A61B 5/053* (2013.01); *A61B 5/1451* (2013.01); *A61B 5/4881* (2013.01); *A61B 5/6828* (2013.01); *A61B 5/6843* (2013.01); *A61B 5/7225* (2013.01); *A61M 1/28* (2013.01); *G16H 50/20* (2018.01); *A61B 5/02* (2013.01); *A61M 2205/3303* (2013.01); *A61M 2230/65* (2013.01); *G06F 17/18* (2013.01)

(56) References Cited

U.S. PATENT DOCUMENTS

| | | | | |
|---|---|---|---|---|
| 2009/0043222 A1* | 2/2009 | Chetham | | A61B 5/4878 600/547 |
| 2010/0152605 A1* | 6/2010 | Ward | | A61B 5/4878 600/547 |
| 2011/0251513 A1* | 10/2011 | Chetham | | A61B 5/0537 600/547 |

FOREIGN PATENT DOCUMENTS

| | | |
|---|---|---|
| WO | 02089668 A2 | 11/2002 |
| WO | 02089669 A | 11/2002 |
| WO | 2015048639 A1 | 4/2015 |

OTHER PUBLICATIONS

T. A. Manzone, H, Q. Dam, D. Soltis and V.V. Sagar, "Blood volume analysis: a new technique and new clinical interest reinvigorate a classic study" J Nucl Med Technol, vol. 35, pp. 55-63, 2007.

S. Abbas, F. Zhu and N. Levin, "Bioimpedance can solve problems of fluid overload." J Ren Nutr., vol. 25, pp. 234-237, 2015.

F. Zhu, P. Kotanko, S. Thijssen and N.W. Levin, "Prediction of Intradialytic Morbid Events in Hemodialysis Patients by Monitoring the Second Derivative of Relative Blood Volume" Proceedings of the 34th IEEE EMBS Annual International Conference San Diego, USA, pp. 1226-1229, 2012.

F. Zhu, P. Kotanko, G.J. Handelman, J.G Raimann, L. Liu, M. Carter, M. Kuhlmann, E. Seibert, E.F. Leonard, N.W. Levin, "Estimation of normal hydration in dialysis patients using whole body and calf bioimpedance analysis" Physiol. Meas. vol. 32, pp. 887-902, 2011.

Nylin, G. and Celander, H., "Determination of Blood Volume in the Heart and Lungs and the Cardiac Output through the Injection of Radiophosphorus" Circulation 1(1): 76-80 (1950).

Schneditz, et al., "Concordance of absolute and relative plasma volume changes and stability of Fcells in routine hemodialysis", Hemodialysis International 20(1):120-128 (2016).

S. Kron, et al., "Vascular refilling is independent of volume overload in hemodialysis with moderate ultrafiltration requirements", Hemodialysis International 20(3): 484-491 (2016).

Geer, et al., "Faster rate of blood volume change in pediatric hemodialysis patients impairs cardiac index", Pediatric Nephrology, 32(2): 341-345 (2017).

Wiig, H. and Reed, R.K., "Volume pressure relationship (compliance) of interstitium in dog skin and muscle", American Journal of Physiology 253(2): H291-H298 (1987).

International Search Report and Written Opinion for application No. PCT/US2018/041474, dated Oct. 18, 2018, 12 pages.

Communication pursuant to Article 93(3) EPC, for Application No. EP18746811.1, dated Jul. 12, 2021, 6 pages.

* cited by examiner

TECHNIQUES FOR DETERMINING FLUID VOLUMES USING BIOIMPEDANCE INFORMATION

CROSS-REFERENCE TO RELATED APPLICATION

This application claims priority to U.S. Provisional Patent Application Ser. No. 62/531,254, filed on Jul. 11, 2017, entitled "Estimation of Peripheral Blood Volume and Interstitial Volume in Hemodialysis Patients Using Bioimpedance Techniques," the contents of which are incorporated herein by reference.

TECHNICAL FIELD

Embodiments herein generally relate to processes and apparatuses operative to determine fluid volumes of a patient, such as interstitial fluid volume and peripheral blood volume, based on bioimpedance information obtained under varying conditions.

BACKGROUND

Monitoring fluid statuses of dialysis patients is necessary to successfully manage patient outcomes. For example, measurements of blood volume and interstitial fluid volume are important for understanding fluid dynamics during hemodialysis (HD). In HD treatment, ultrafiltration (UF) may be applied to remove excess fluid from the interstitial fluid volume ($V_{IT}$) via the blood volume (BV) compartment. Since it is difficult to set an appropriate UF rate (UFR) for an individual treatment without a target of known normal fluid status, rapid reduction in BV by a high UFR can result in complications for the patient, such as intradialytic hypotension (IDH). In addition, chronic fluid overload may lead to various circulatory system and heart conditions.

Conventional fluid volume monitoring methods may be inefficient and difficult to implement in a clinical setting. For example, one conventional technique for measurement of absolute blood volume is tracer dilution. However, this technique may be time consuming and requires the use of a tracer, usually a radioisotope, which is typically challenging to implement in a clinical setting. Another example conventional technique is relative blood volume (RBV), which may lack precision and accuracy as that technique is only able to provide relative changes in fluid volume.

Accordingly, monitoring fluid volumes may facilitate safe dialysis treatment. It is with these considerations in mind that the present disclosure may be useful.

SUMMARY

In accordance with various aspects of the described embodiments is an apparatus, comprising at least one memory, and logic coupled to the at least one memory, the logic to receive baseline bioimpedance information for at least a portion of a human body at a baseline pressure, receive pressurized bioimpedance information of the portion of the human body at a pressurized pressure, the pressurized pressure greater than the baseline pressure and configured to substantially remove blood volume from the portion at the pressurized pressure, and determine at least one of interstitial fluid volume ($V_{IT}$) or peripheral blood volume ($BV_P$) based on the baseline bioimpedance information and the pressurized bioimpedance information.

In some embodiments of the apparatus, the portion includes a calf. In various embodiments of the apparatus, the baseline bioimpedance information may be generated via at least one of whole body bioimpedance spectroscopy (wBIS) or calf bioimpedance spectroscopy (cBIS). In some embodiments of the apparatus, the baseline pressure may be about 0 mmHg. In exemplary embodiments of the apparatus, the pressurized pressure may be about a systolic blood pressure (SBP). In various embodiments of the apparatus, the logic may determine extracellular volume (ECV) based on the baseline bioimpedance information, and determine $V_{IT}$ based on ECV and the pressurized bioimpedance information. In some embodiments of the apparatus, the logic may determine total body water (TBW) based on the baseline bioimpedance information, and determine $BV_P$ based on TBW and the pressurized bioimpedance information. In various embodiments of the apparatus, the pressurized bioimpedance information may be generated by performing calf bioimpedance spectroscopy (cBIS) on a calf of the human body pressurized by a blood pressure cuff.

In some embodiments of the apparatus, the logic may determine $V_{IT}$ according to the following:

$$V_{IT} = ECV\left(\frac{R_{0,E}}{R_{P,E}}\right),$$

where $R_{0,E}$ a first resistance value at the baseline pressure and a low current frequency and $R_{P,E}$ is a second resistance value at the pressurized pressure and a low current frequency. In various embodiments of the apparatus, the logic may determine $BV_P$ according to the following:

$$BV_P = TBW\left(1 - \frac{R_{0,T}}{R_{P,T}}\right),$$

where $R_{0,T}$ is a first resistance value at the baseline pressure and a high current frequency and $R_{P,T}$ is a second resistance value at the pressurized pressure and a high current frequency.

In accordance with various aspects of the described embodiments is a method including determining baseline bioimpedance information for at least a portion of a human body at a baseline pressure, determining pressurized bioimpedance information of the portion of the human body at a pressurized pressure, the pressurized pressure greater than the baseline pressure and configured to substantially remove blood volume from the portion at the pressurized pressure, and determining at least one of interstitial fluid volume ($V_{IT}$) or peripheral blood volume ($BV_P$) based on the baseline bioimpedance information and the pressurized bioimpedance information.

In some embodiments of the method, the portion may include a calf. In some embodiments of the method, the baseline bioimpedance information may be generated via at least one of whole body bioimpedance spectroscopy (wBIS) or calf bioimpedance spectroscopy (cBIS). In some embodiments of the method, the baseline pressure may be about 0 mmHg. In some embodiments of the method, the pressurized pressure may be about a systolic blood pressure (SBP). In some embodiments, the method may include determining extracellular volume (ECV) based on the baseline bioimpedance information, and determining $V_{IT}$ based on ECV and the pressurized bioimpedance information. In some embodiments, the method may include determining total body water (TBW) based on the baseline bioimpedance information, and determining $BV_P$ based on TBW and the pressurized bioimpedance information. In some embodiments of the method, the pressurized bioimpedance information may be generated by performing calf bioimpedance spectroscopy (cBIS) on a calf of the human body pressurized by a blood pressure cuff.

In some embodiments, the method may include determining $V_{IT}$ according to the following:

$$V_{IT} = ECV\left(\frac{R_{0,E}}{R_{P,E}}\right),$$

where $R_{0,E}$ is a first resistance value at the baseline pressure and a low current frequency and $R_{P,E}$ is a second resistance value at the pressurized pressure and a low current frequency. In some embodiments, the method may include determining $BV_P$ according to the following:

$$BV_P = TBW\left(1 - \frac{R_{0,T}}{R_{P,T}}\right),$$

where $R_{0,T}$ is a first resistance value at the baseline pressure and a high current frequency and $R_{P,T}$ is a second resistance value at the pressurized pressure and a high current frequency.

DETAILED DESCRIPTION

Figure 1:
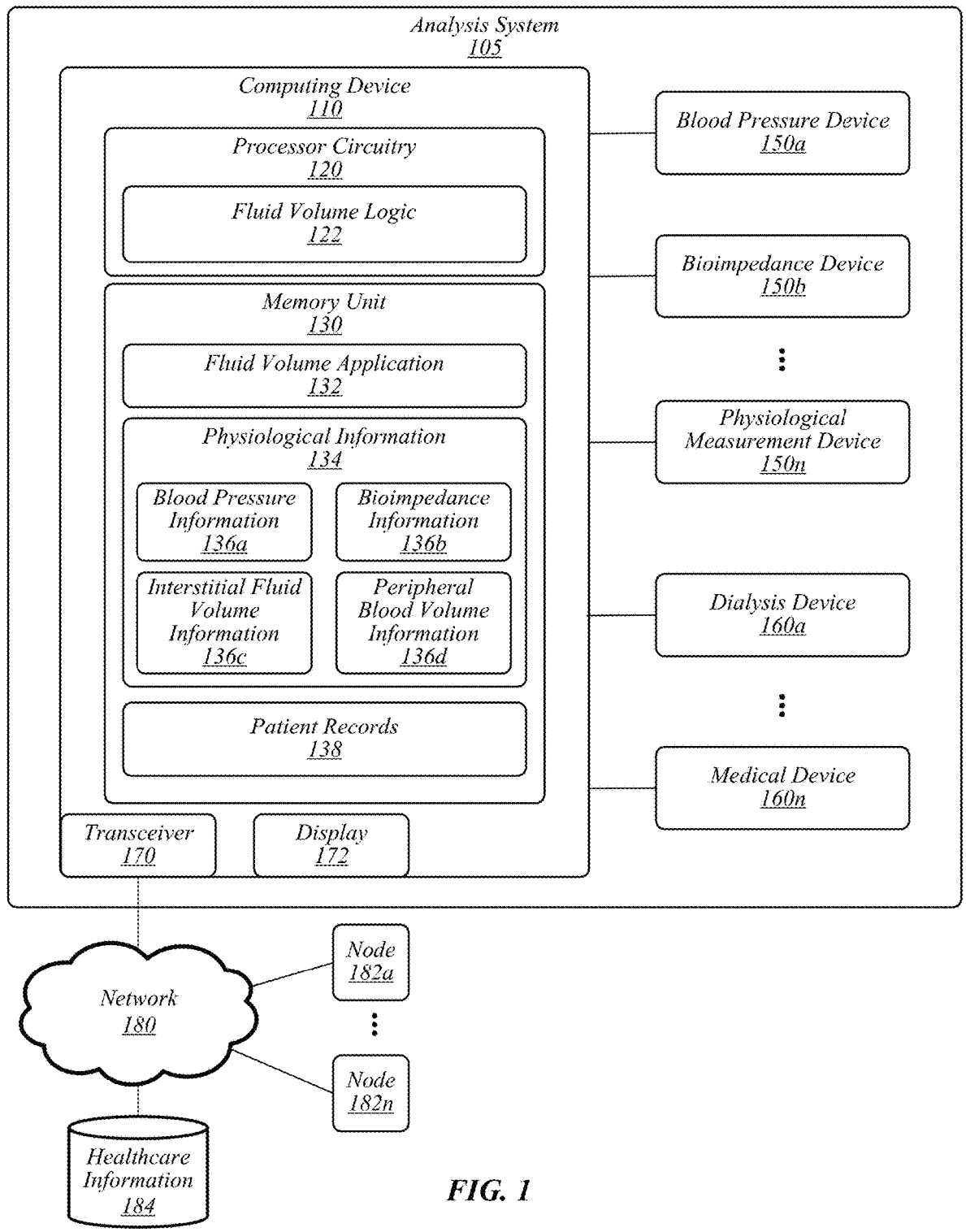
FIG. 1 illustrates an embodiment of a first operating environment.

Various embodiments may generally be directed toward systems, methods, and/or apparatus for determining fluid volumes based on bioimpedance information. In some embodiments, the fluid volumes may include at least one of interstitial fluid volume ($V_{IT}$) and blood volume (BV), for example, of a peripheral portion of the human body (peripheral BV ($BV_P$)). In various embodiments, the bioimpedance information may include at least one of whole-body bioimpedance or bioimpedance of a portion of a human body, such as calf bioimpedance. In exemplary embodiments, the bioimpedance information may be obtained via bioimpedance spectroscopy (BIS), for example, whole-body bioimpedance information may be obtained via whole-body bioimpedance spectroscopy (wBIS), calf bioimpedance information may be obtained via calf bioimpedance spectroscopy (cBIS), and/or the like.

In general, BIS techniques are used to estimate certain body fluid volumes by injecting current and measuring resistance and reactance by placement of electrodes on the surface of the skin of an area of interest. Low frequency current (for instance, about 0.1 kHz to about 5 kHz) passes through the extracellular volume (ECV) and high frequency current (for instance, about 1000 kHz) passes through both extracellular and intracellular (ICV) volumes. In this manner, BIS may provide ECV, ICV and total body water (TBW) information. However, conventional BIS techniques cannot separate plasma volume (PV) and $V_{IT}$ from ECV, or separate whole blood volume (BV) from TBW.

In some embodiments, BIS may be performed at a baseline blood pressure (i.e., non-pressurized) to determine baseline bioimpedance information. The baseline bioimpedance information may be determined at multiple frequencies, such as a low frequency (i.e., about 5 kHz) and/or a high frequency (i.e., about 1000 kHz) to determine ECV and TBW, respectively. Pressure may be applied to a portion of the human body, for example, to a calf via a blood pressure cuff or other device for a pressure duration. Application of pressure to the portion of the human body may operate to remove or substantially remove blood volume from the portion of the human body. In some embodiments, the blood pressure device may operate to pressurize the portion of the human body to a systolic blood pressure (SBP). In some embodiments, SBP may be about 110 mmHg, about 120 mmHg, about 125 mmHg, about 130 mmHg, about 80 mmHg to about 140 mmHg, about 110 mmHg to about 130 mmHg, about 120 mmHg, or any value or range between any of these values or ranges (including endpoints). BIS may be performed on the portion of the human body during the pressure duration to determine pressurized bioimpedance information under conditions that exclude or substantially exclude blood volume from the portion of the human body. The pressurized bioimpedance information may be used to determine $V_{IT}$ from ECV and/or BV (such as $BV_P$) from TBW according to some embodiments.

Accordingly, embodiments may operate to provide multiple technological advantages over conventional systems for determining and/or estimating fluid volumes. For example, a non-limiting technological advantage includes determining $V_{IT}$ based on bioimpedance information by separating $V_{IT}$ from ECV. In another example, a non-limiting technological advantage includes determining BV based on bioimpedance information by separating blood volume (BV) from TBW, for instance, in a portion of the human body to determine $BV_P$.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In this Detailed Description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include an analysis system 105 operative to manage physiological analysis of a patient. In various embodiments, analysis system 105 may include computing device 110 communicatively coupled to one or more physiological measurement devices 150a-n and/or medical devices 160a-n, or otherwise configured to receive and store data therefrom, such as blood pressure information 136a, bioimpedance information 136b, and/or the like. For example, physiological measurement devices 150a-n and/or medical devices 160a-n may operate to provide data to a location on a network 150 (for instance, a cloud computing environment), such as nodes 182a-n, healthcare information database 184, and/or the like, accessible to computing device 110. In some embodiments, computing device 110 may be operative to control, monitor, manage, or otherwise process various operational aspects of physiological measurement devices 150a-n and/or medical devices 160a-n. In some embodiments, computing device 110 may be or may include a stand-alone computing device, such as a personal computer (PC), server, tablet computing device, cloud computing device, smartphone, tablet computing device, and/or the like. In some embodiments, computing device 110 may be an embedded computing device in one or more of physiological measurement devices 150a-n and/or medical devices 160a-n.

As shown in FIG. 1, computing device 110 may include processing circuitry 120, a memory unit 130, a transceiver 170, and/or a display 172. Processing circuitry 120 may be communicatively coupled to memory unit 130, transceiver 170, and/or display 172.

Figure 13:
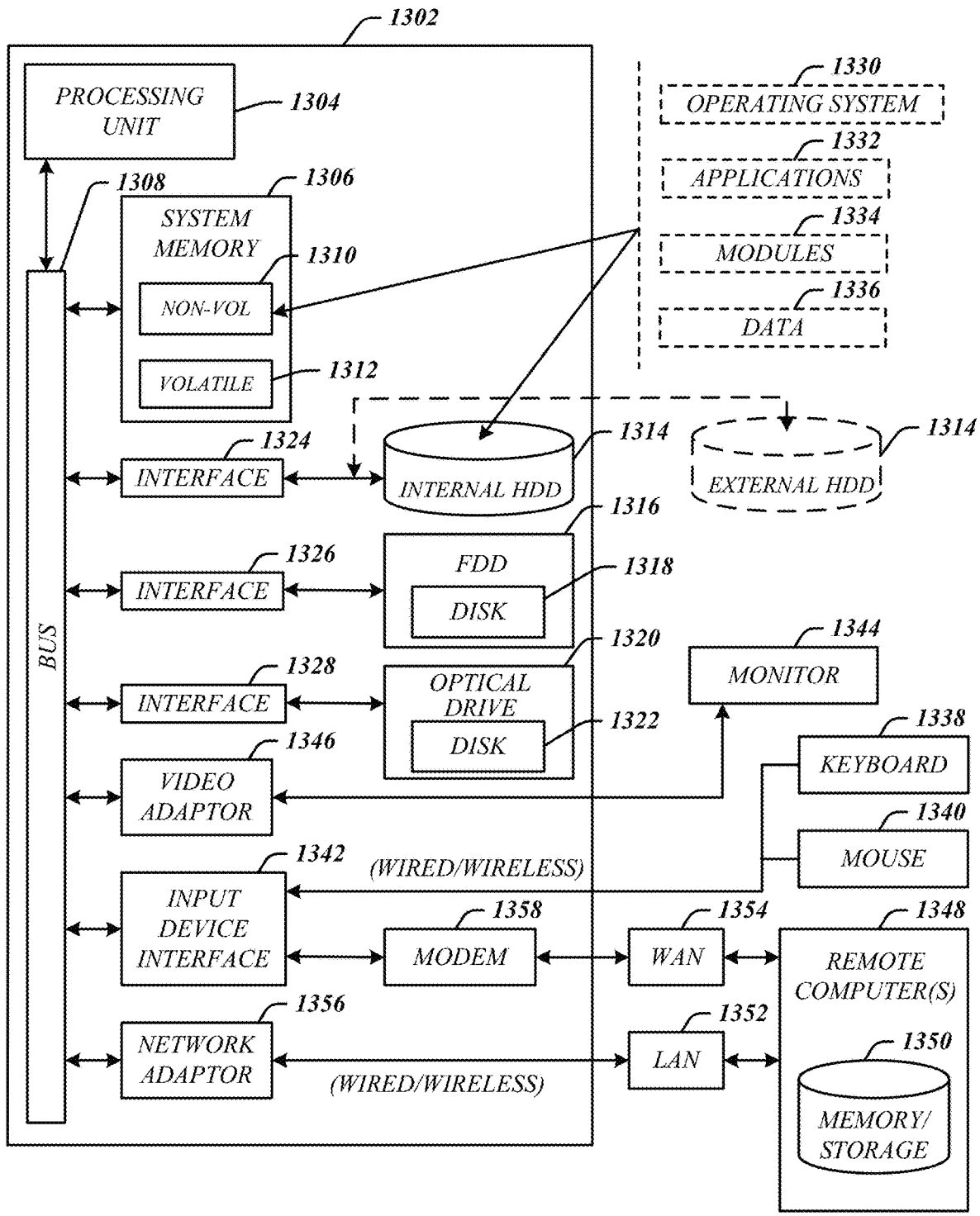
FIG. 13 illustrates an embodiment of a computing architecture.

Processing circuitry 120 may include and/or may access various logic for performing processes according to some embodiments. For instance, processing circuitry 120 may include and/or may access fluid volume logic 122. Processing circuitry and/or fluid volume logic 122, or portions thereof, may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1300 (FIG. 13). For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although fluid volume logic 122 is depicted in FIG. 1 as being within processing circuitry 120, embodiments are not so limited. For example, fluid volume logic 122 may be located within an accelerator, a processor core, an interface, an individual processor die, implemented entirely as a software application (for instance, fluid volume application 132) and/or the like.

In some embodiments, physiological measurement devices 150a-n may include various devices operative to measure physiological characteristics of a patient. Non-limiting examples of physiological devices 150a-n may include a blood pressure device 150a and a bioimpedance device 150b. Although a blood pressure device 150a and a bioimpedance device 150b may be used as illustrative physiological measurement devices 150a-n, embodiments are not so limited, as physiological measurement devices 150a-n may include any type of device capable of measuring physiological information of a patient.

In general, a blood pressure device 150a may be or may include a blood pressure cuff and associated elements for applying pressure to a portion of a human body. In some embodiments, blood pressure device 150a may generate blood pressure information 136a resulting from measuring the applied pressure and/or blood pressure of the portion of the human body. Computing device 110 may access information blood pressure information 136b associated with the operation of blood pressure device 150a from memory unit 130, healthcare information database 184, nodes 182a-n, and/or the like.

In various embodiments, bioimpedance device 150b may include a device operative to measure bioimpedance information 136b associated with a human body. For example, bioimpedance device 150b may include a stimulating system which applies a current (for instance, an AC current) at two spaced apart locations on a patient (for instance, the surface of a patient's calf for a calf bioimpedance analysis or on the wrist, foot, ankle, and/or the like for a whole body bioimpedance analysis) and a recording system operative to detect the resulting voltage (for instance, AC voltage) difference at the two spaced apart locations. The voltage difference may then be used to calculate a bioimpedance value or, in some cases, simply a resistance (R) value. In some embodiments, bioimpedance device 150b may be operative to perform BIS, such as wBIS and/or cBIS. In exemplary embodiments, bioimpedance device 150b may operate at various currents or current frequencies (for instance, to perform multi-current BIS).

The degree of conduction of current through the intracellular compartment is frequency dependent due to the presence of the cell membrane that exhibits similar electrical properties to those of an electrical capacitor. Since the potential difference developed across the tissue also undergoes a phase shift with respect to the applied current (due to the cell membrane), the overall measurement is known as the "impedance," signifying the dependence on frequency. An application of low frequency alternating current causes conduction almost exclusively through the extracellular spaces of the tissues. In a low frequency range, the cell membrane behaves as an insulator inhibiting the passage of current. In the high frequency range, the cell membranes conduct and current passes through both the intracellular and extracellular spaces.

By analysis of the impedance and phase shift at different frequencies, the resistance of the extracellular water volume (ECV; $R_E$) and intracellular water volume (ICV; $R_I$) of the body tissue may be derived. The values of both $R_E$ and $R_I$ depend on the volume of fluid in the respective tissue compartments. By combining anthropometric measurements of body segments and tissue resistivity constants determined, for example, from dilution studies, ECV and ICV may be calculated.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store a fluid volume application 132 that may operate, alone or in combination with fluid volume logic 122, to perform various functions for determining fluid volumes according to some embodiments. In some embodiments, fluid volume application 132 may include application programming interfaces (APIs) and/or graphical user interfaces (GUIs) to read, write, and/or otherwise access physiological information 134 and/or patient records 138, such as via display 172 and/or corresponding displays of physiological measurement devices 150a-n, medical devices 160a-n, nodes 182a-n, web interfaces, mobile application ("mobile applications," "mobile apps," or "apps"), and/or the like. In this manner, in some embodiments, an operator may search, visualize, read, add to, or otherwise access physiological data, patient records, and/or the like. In various embodiments, an operator may perform an analysis to determine fluid volumes, operate physiological measurement devices 150a-n, medical devices 160a-n, and/or the like.

In various embodiments, fluid volume application 132 (which may be or may be included within fluid volume logic 122) may operate to implement or facilitate a fluid volume process. The fluid volume process may include processes for obtaining physiological data 135 and to determine fluid volumes 136c, 136d according to the physiological data 135 (see, for example, FIG. 4). In some embodiments, fluid volume application 132 may automatically operate blood pressure device 150a in combination with bioimpedance device 150b, for instance, according to a process programmed according to exemplary embodiments, to obtain blood pressure information 136a and bioimpedance information 136b. In various embodiments, an operator may operate blood pressure device 150a in combination with bioimpedance device 150b, for instance, according to a process of some embodiments, to obtain blood pressure information 136a and bioimpedance information 136b. In exemplary embodiments, blood pressure device 150a or bioimpedance device 150b may be wholly or partially operated by fluid volume application 132, and the other of blood pressure device 150a or bioimpedance device 150b may be wholly or partially operated by an operator. Blood pressure information 136a and/or bioimpedance information 136b may be automatically transmitted to computing device 110, entered by the operator, or some combination thereof. Embodiments are not limited in this context.

In some embodiments, blood pressure device 150a and bioimpedance device 150b may be operated to perform a fluid volume analysis. For example, bioimpedance device 150b may be operated to generate baseline bioimpedance information (for instance, wBIS and/or cBIS under normal or non-pressurized conditions) during a first phase of the fluid volume analysis. Blood pressure device 150a may be activated to pressurize a portion of the patient, such as the calf, at a specified pressure for a specified duration. The specified pressure may be selected to ensure that at least a region of the portion of the patient is devoid or substantially devoid of blood volume, sufficient to generate pressurized bioimpedance information (for instance, BIS in a region devoid or substantially devoid of blood volume). In various embodiments, the specified pressure may be about systolic blood pressure (SBP). In some embodiments, substantially devoid of blood volume may include the region being reduced of blood volume by about 50%, about 60%, about 70%, about 80%, about 85%, about 90%, about 95%, about 99%, about 100%, and any value or range between any two values (including endpoints). In some embodiments, substantially devoid of blood volume may include a blood pressure device pressure equal to or greater than a pressure that, when increased, does not result in a material change in BIS resistance (see, for example, FIG. 7). In some embodiments, the region being pressurized (for instance, devoid or substantially devoid of blood volume) may be or may include a region in which bioimpedance information is being measured (for instance, between two stimulating electrodes of a bioimpedance device (see, for example, FIG. 5)). Bioimpedance device 150a may be operated under pressurized conditions on the portion of the human body to determine pressurized bioimpedance information.

In various embodiments, fluid volume application 132 may perform the fluid volume analysis to determine ECV and/or TBW based on the baseline bioimpedance information. In some embodiments, fluid volume application 132 may perform the fluid volume analysis to determine $V_{IT}$ and/or $BV_P$ based on ECV and TBW, respectively, and the pressurized bioimpedance information using one or more of Equations (1)-(7) described below. In various embodiments, $V_{IT}$ and/or $BV_P$ may be stored as physiological information 134, such as interstitial fluid volume information 136c and/or peripheral blood volume information 136d, respectively.

In some embodiments, fluid volume application 132 may read, write, create, or otherwise access patient records 138. In various embodiments, patient records 138 may be stored in healthcare information database 184, which may be or may include a hospital information management system (HIMS), laboratory information management system (LIMS), Health Information System (HIS), electronic medical records (EMR), and/or the like. In various embodiments, the physiological information 134 may be used to operate one or more of medical devices 160a-n. For example, interstitial fluid volume information 136c and/or peripheral blood volume information 136d may be used to control an operating process for a dialysis device performing HD for a patient to monitor or control the fluid status of the patient. Embodiments are not limited in this context.

Figure 2:
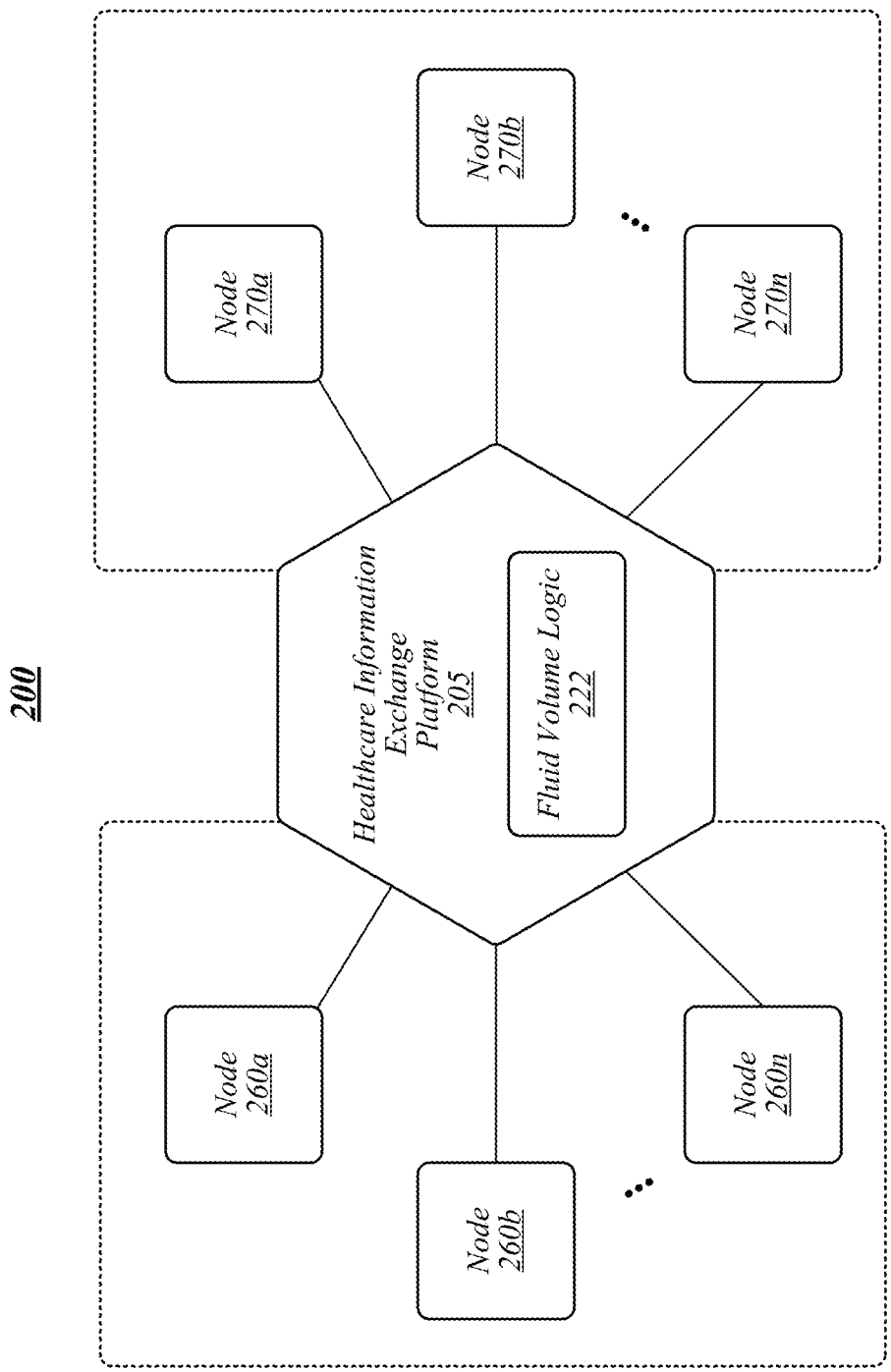
FIG. 2 illustrates an embodiment of a second operating environment.

FIG. 2 illustrates an example of an operating environment 200 that may be representative of some embodiments. As shown in FIG. 2, operating environment 200 may include a healthcare information exchange platform (or a medical device platform) 205. In some embodiments, healthcare information exchange platform 205 may be operative to provide for the exchange of healthcare information among interested entities. In various embodiments, healthcare information exchange platform 205 may include an application platform operative to provide data exchange services among nodes 260a-n and 270a-n. In exemplary embodiments, healthcare information exchange platform 205 may be a software platform, suite, set of protocols, and/or the like provided to customers by a manufacturer and/or developer ("developer") associated with medical devices, medical care services, clinical research services, laboratory services, and/or the like.

For example, a developer may provide healthcare information exchange platform 205 as a data exchange interface for medical devices and/or medical device services. For example, one or more of nodes 270a-n may include a dialysis medical device. An entity, such as a hospital, dialysis clinic, or other healthcare provider providing services to patients using a medical device node 270a-n provided by developer may use healthcare information exchange platform 205 to implement processes according to some embodiments, such as a fluid volume analysis via fluid volume logic 222. Other entities, may access healthcare information exchange platform 205 via a GUI, such as a client application, web interface, mobile app, and/or the like, to perform functions associated with fluid volume logic 222. In some embodiments, at least a portion of healthcare information exchange platform 205 may be hosted in a cloud computing environment.

Nodes 270a-n may be data producers for fluid volume logic 222 and nodes 260a-n may be data consumers of fluid volume logic 222. For example, node 270a-n may include dialysis devices, blood pressure devices, bioimpedance devices, and/or other data producers. Nodes 260a-n may include third-party applications, decision makers, analysis processes, regulators, and/or other data consumers. An entity may be both a data producer and a data consumer.

For example, nodes 270a and 270b may be a blood pressure device and a bioimpedance device operative to function according to some embodiments. Data generated by node 270a and/or 270b may be provided to fluid volume logic 222 for processing, for example, such as baseline bioimpedance information, blood pressure information, pressurized bioimpedance information, and/or the like. Fluid volume logic 222 may use the information from nodes 270a and/or 270b to generate fluid volume information, such as $V_{IT}$ and/or $BV_P$ according to some embodiments. The fluid volume information may be provided to one or more of nodes 260a-n, such as a hospital, HIMS, HIS, LIS, EMR, and/or the like. For example, the fluid volume information may be used by a hospital, clinic, dialysis center, or doctor's office to treat a patient, such as determining operating parameters for a dialysis machine and/or monitoring patient fluid status during performance of dialysis on the patient. In another example, the fluid volume information may be used by a clinical researcher to evaluate dialysis procedures performed in a clinic. Embodiments are not limited in this context.

In some embodiments, healthcare information exchange platform 205 may operate according to a cloud-based model and/or an "as-a-Service" model. In this manner, healthcare information exchange platform 205 may provide for a service that operates as a single, central platform that allows entities to access fluid volume information, bioimpedance information, blood pressure information, patient records, and/or the like to perform healthcare services, research, and/or the like.

Figure 3:
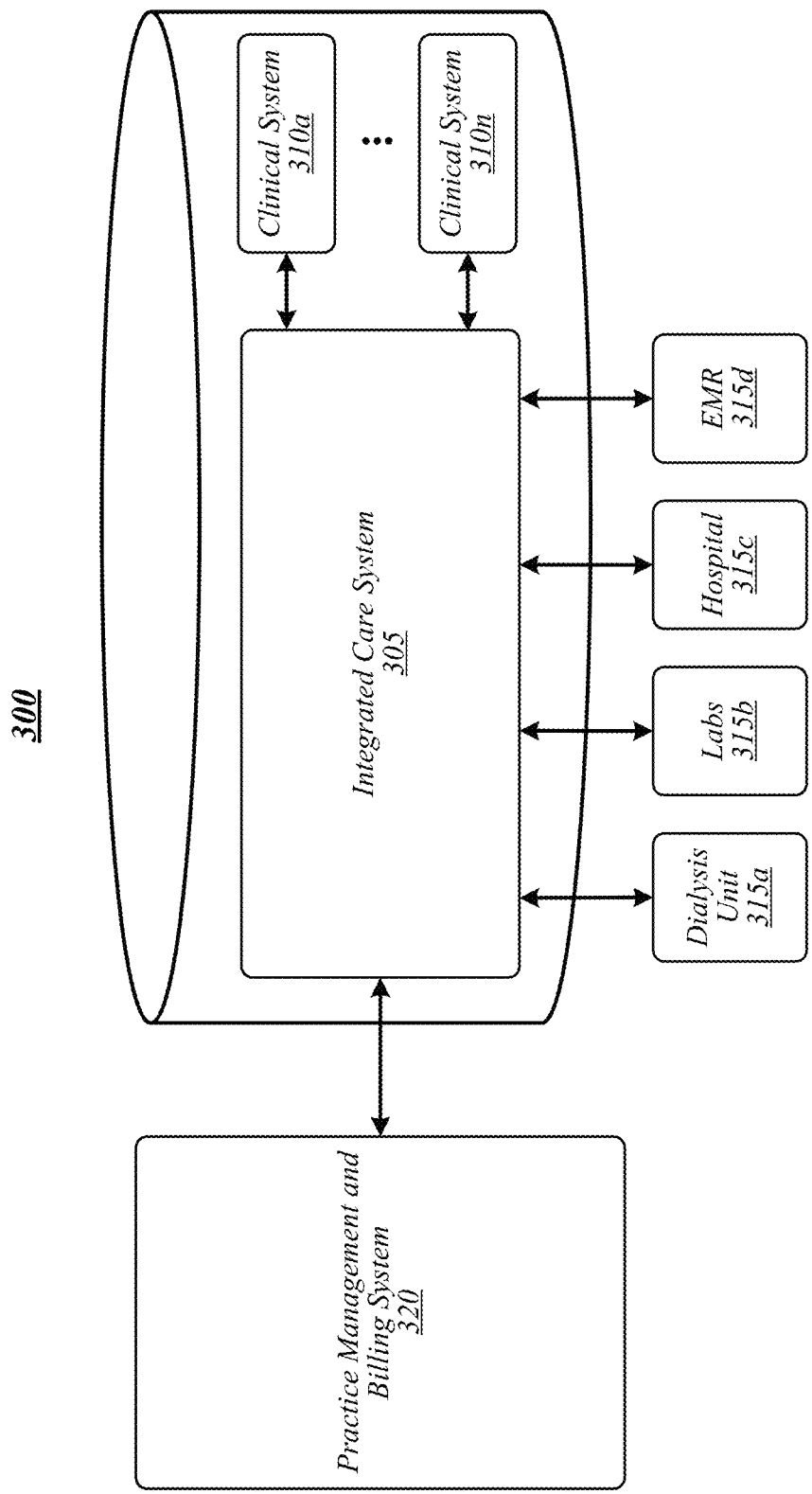
FIG. 3 illustrates an embodiment of a third operating environment.

FIG. 3 illustrates an example of an operating environment 300 that may be representative of some embodiments. As shown in FIG. 3, operating environment 300 may include an integrated care system 305 that may form a part of a clinical system for treating a patient in all aspects of care. In some embodiments, integrated care system 305 may include a specific implementation of healthcare information exchange platform 205.

Integrated care system 305 may be connectable to additional clinical systems 310a-n, including but not limited to a pharmacy, an End-Stage Renal Disease (ESRD) and/or Chronic Kidney Disease (CKD) data registry, a hospital, a dialysis clinic, a renal and/or kidney disease research facility, and/or the like. For example, integrated care system 305 may automatically send prescriptions and other patient information to a pharmacy based on information provided by a medical professional, and may be able to send and receive data and information to the CKD/ESRD data registry, for comparison to other patients and projections for future treatment. In another example, integrated care system 305 may determine and/or access fluid volume information. Integrated care system 305 may determine events associated with CKD/ESRD and take appropriate action, including but not limited to informing patients, informing clinicians of when specific interventions are warranted, and/or alerting clinicians to upcoming important dates for interventions.

One or more outside systems 315a-d may also be connectable to integrated care system 305. For example, the outside systems 315a-d may include one or more of a dialysis unit (or dialysis machine) 315a, labs 315b, doctor's office and/or hospital 315c, and/or electronic medical records (EMR) 315d. Patient information, including fluid volume information and/or information used to generate fluid volume information, may be sent and received between integrated care system 305 and the outside systems 315a-n, so that patient care and/or research may be more efficient, standardized, and consistent across several functions. For example, integrated care system 305 may receive information from a patient's electronic medical records, thereby accessing historical information. Dialysis unit 315a, labs 315b, doctor's office or hospital 315c, EMR 315d, and/or the like may send and receive information to and from integrated care system 305 based on patient treatment.

As described below with respect to FIGS. 11 and 12, in some embodiments, integrated care system 305 may provide information to a dialysis machines 1100 and/or 1200 for use in dialysis treatment. In some embodiments, integrated care system 305 may send the dialysis machine 1100 and/or 1200 a prescription from a medical professional for a prescribed dialysis treatment, in which case integrated care system 305 may receive the prescription from a doctor's office or hospital. Integrated care system 305 may also be able to verify the prescribed treatment against the patient's lab work or medical records. In some embodiments, integrated care system 305 may determine and/or obtain, such as from labs 315b, EMR 315d, and/or the like, fluid volume information such as $V_{IT}$ and/or $BV_P$ determined according to various embodiments for a patient. In exemplary embodiments, integrated care system 305 may remotely program the prescription and/or fluid volume information onto the patient's dialysis machine and/or forward the prescription and/or fluid volume information to the machine for local set-up. In this manner, the patient may be sure to receive the necessary and correct treatment and may be prevented from administering or receiving an improper amount of dialysis treatment, thereby reducing human error and improving patient care.

Integrated care system 305 may also be able to inform the relevant medical professional based on information received from these outside systems 315a-n, as well as the additional clinical systems 310a-n, to provide appropriate medical treatment to the patient, including course(s) of treatment that may lessen or avoid a risk of hospitalization.

Figure 4:
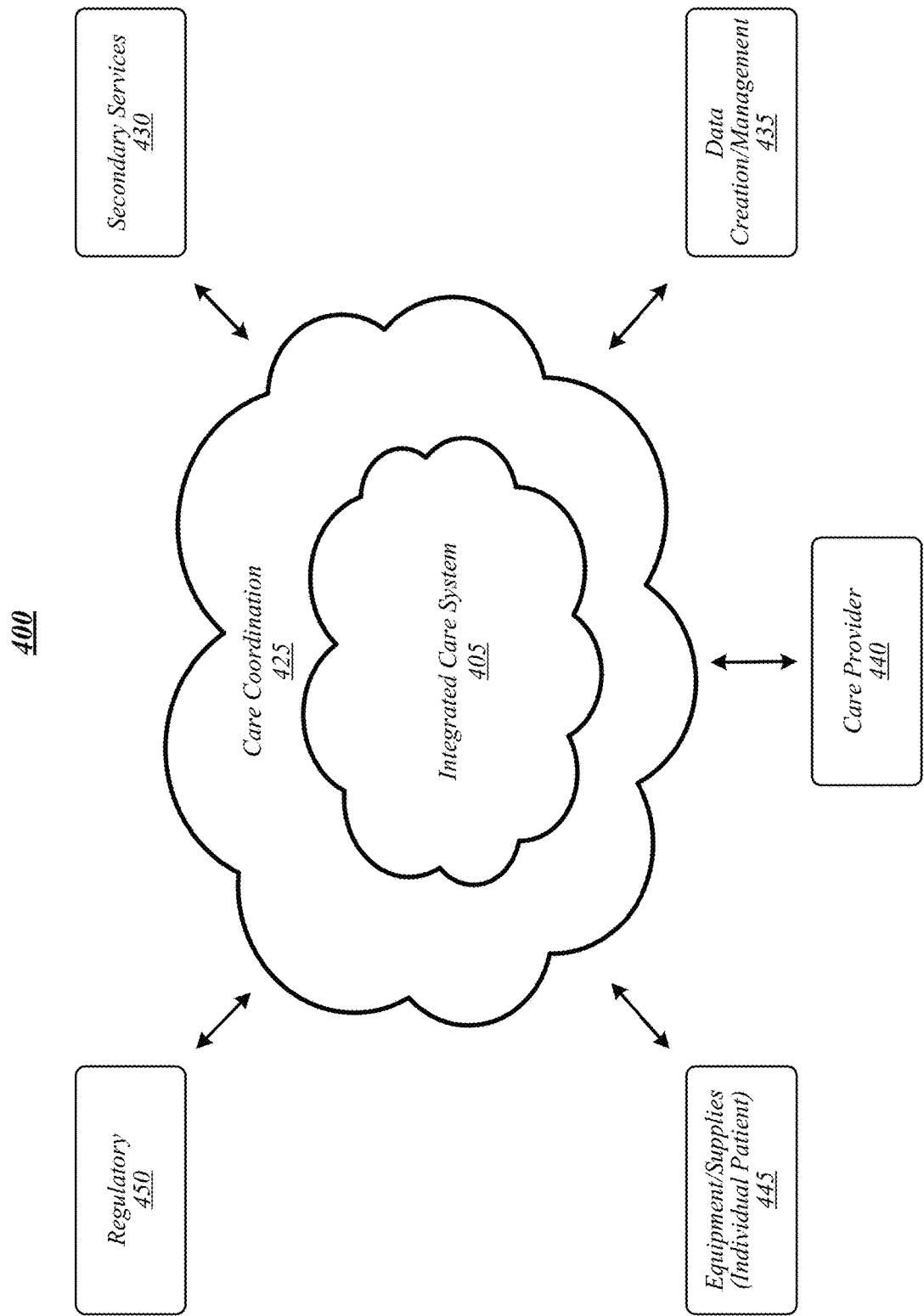
FIG. 4 illustrates an embodiment of a fourth operating environment.

FIG. 4 illustrates an example of an operating environment 400 that may be representative of some embodiments. As shown in FIG. 4, operating environment 400 may include a system of integrating patient care for use in treating kidney disease, for example, ESRD and/or CKD. In some embodiments, operating environment 400 may show additional details, including additional components and enumerations, and/or an expanded architecture, for example, of operating environment 300. For example, the population of patients diagnosed with ESRD have been increasing over time, often caused by several other diseases, including but not limited to diabetes, hypertension, and/or glomerulonephritis. Patients living with ESRD may face additional challenges due to the nature of the disease, for example, required lifestyle changes may lead to mental health deterioration. Additionally, at-home treatments may lead to increased isolation from medical professionals. As the healthcare landscape changes, opportunities to provide patients with resources for coordinating treatment may deliver additional patient health benefits beyond dialysis treatment.

In various embodiments, integrated care system 405 may integrate various healthcare models, for example, Accountable Care Organizations (ACO's), ESRD Seamless Care Organizations (ESCO's), Chronic Special Needs Plans (C-SNP's), and/or the like. Care coordination unit 425 may coordinate with integrated care system 405 to oversee and manage patient care. Various components may engage within integrated care system 405 to provide complete patient care via a care coordination unit 425. For example, any number of integrated care components may send and receive information to and from integrated care system 405, including but not limited to a secondary services component 430, a data creation and/or management component 435, a care provider component 440, an equipment and/or supplies component 445, a regulatory component 450, and/or the like.

Each component of an integrated care system 405 may include one or more units, including internal services and support as well as external services and support. In some embodiments, secondary services component 430 may include any number of services including, without limitation, laboratory services, personalized care services, and/or pharmacy services. Each of secondary services 430 may send and receive patient information to integrated care system 405 for compilation and analysis. For example, a laboratory may automatically send results of patient bloodwork and other test results to integrated care system 405. In another example, a clinic may automatically send fluid volume information determined according to some embodiments to integrated care system 405. Additionally, integrated care system 405 may automatically send testing instructions to the laboratory for selected tests on patient samples, based on determinations from medical professionals, and/or other information gathered by care coordination unit 425, such as fluid volume information. Similarly, integrated care system 405 may automatically send prescriptions and dosage instructions to a pharmacy based on a patient's test results and other factors determined by integrated care system 405. The pharmacy may also send information to integrated care system 405 related to other patient prescriptions for potential adverse drug interactions, how timely a prescription is refilled, and/or patient interaction with the pharmacist, and/or the like.

Figure 5B:
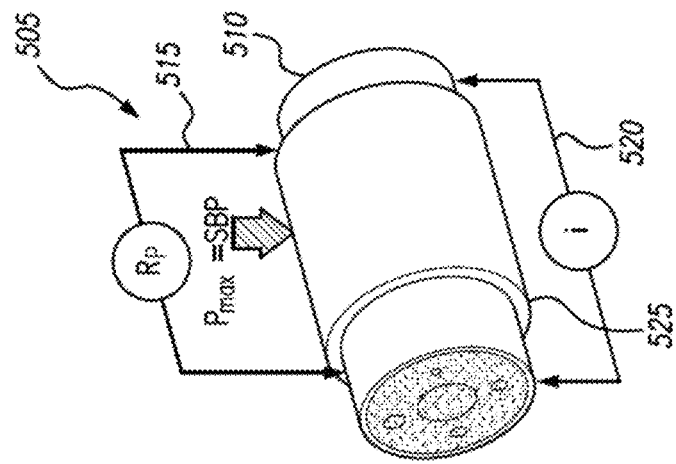
FIGS. 5A and 5B illustrate configurations for performing fluid volume analysis on a portion of a human body according to some embodiments.
Figure 5A:
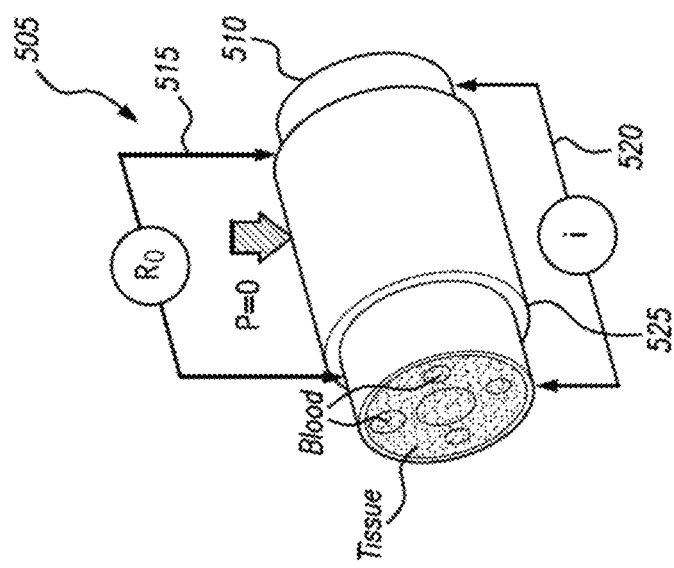

FIGS. 5A and 5B illustrate configurations for performing fluid volume analysis on a portion of a human body according to some embodiments. As shown in FIG. 5A, a bioimpedance system 505 may include a bioimpedance stimulating system 515 arranged in contact with a portion of a human body 510 (for instance, a calf). In various embodiments, stimulating system 515 may apply an AC current at two spaced-apart locations (for instance, stimulating electrodes) on the surface of the calf 510. Bioimpedance system 505 may include a recording system 520 arranged to detect the resulting AC voltage difference at two spaced-apart locations, which, for example, may be inboard of the stimulating locations. The AC voltage difference is then used to calculate a bioimpedance value or, in some cases, simply a resistance (R) value. The procedure can be performed at one frequency, e.g., 5 kilohertz, or as a BIS procedure at a plurality of frequencies. In some embodiments, cBIS may be performed on calf 510. A blood pressure device 525, such as a blood pressure cuff (or "cuff"), may be arranged around calf 510. The cuff 525 may be non-pressurized, as depicted in FIG. 5A, or pressurized, as depicted in FIG. 5B.

In some embodiments, baseline bioimpedance information may be obtained by performing cBIS continuously for a baseline duration with cuff 525 non-pressurized (for instance, pressure (P)=0 or substantially 0) ("baseline BIS" or "baseline cBIS"). In some embodiments, the baseline duration may be about 30 seconds. In various embodiments, the baseline duration may be about 5 seconds, about 10 seconds, about 20 seconds, about 30 seconds, about 1 minute, about 5 minutes, about 10 minutes, about 30 minutes, about 1 hour, and any value or range between any two of these values (including endpoints). Baseline cBIS may be performed at various current frequencies, such as a low frequency of about 5 kHz and a high frequency of about 1000 kHz. In some embodiments, cBIS may be performed at various frequencies, such as about 1 kHz, about 2 kHz, about 5 kHz, about 10 kHz, about 50 kHz, about 100 kHz, about 500 kHz, about 1000 kHz, about 2000 kHz, and any value or range between any two of these values (including endpoints).

In various embodiments, baseline cBIS with 5 kHz ($R_0$, 5) and 1000 kHz ($R_0$, 1000) may represent the resistances in ECV ($R_0$, E) and TBW ($R_0$, T) in the calf respectively. After the baseline duration, pressurized cBIS may be initiated as cBIS is continuously measured as cuff 525 is inflated to a pressurized pressure. In some embodiments, the pressurized pressure may be a non-zero value. In various embodiments, the pressurized pressure may be a systolic blood pressure (SBP). In some embodiments, the pressurized pressure may be a pressure sufficient to remove or substantially remove blood from the portion of the human body 510. In some embodiments, the pressurized pressure may be equal to or greater than a value that, when increased, does not result in a material change in BIS resistance (see, for example, FIG. 7). In some embodiments, the pressurized pressure may be a pressure applied to a body segment. In various embodiments, the pressurized pressure may be a blood pressure of or measured within the body segment. In some embodiments, the pressurized pressure may be about 5 mmHg, about 10 mmHg, about 20 mmHg, about 50 mmHg, about 100 mmHg, about 10 mmHg, about 120 mmHg, about 125 mmHg, about 130 mmHg, about 150 mmHg, about 200 mmHg, about 250 mmHg, about 300 mmHg, about 80 mmHg to about 140 mmHg, about 110 mmHg to about 130 mmHg, about 100 mmHg to about 250 mmHg, about 200 mmHg to about 250 mmHg, and any value or range between any two of these values or ranges (including endpoints).

Figure 6:
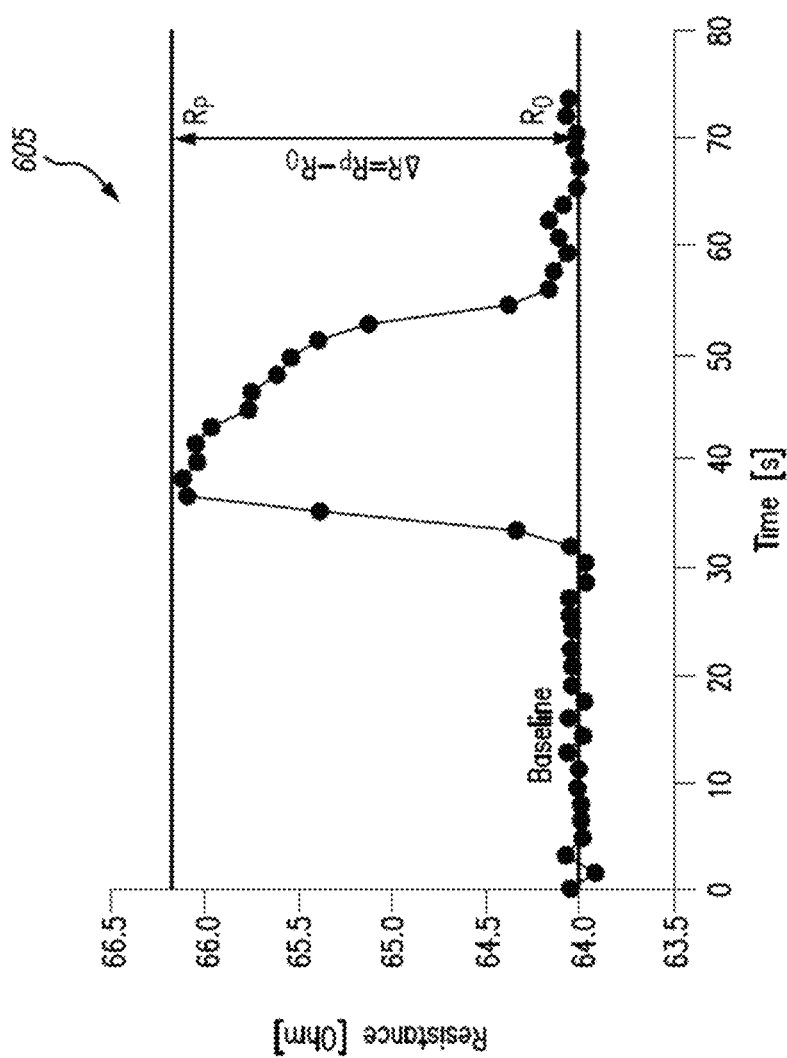
FIG. 6 illustrates a graph depicting an exemplary change in resistance based on a change in blood pressure.

In various embodiments, pressurized cBIS may be performed for a pressurized duration to squeeze blood from calf 510, and then cuff 525 may be deflated to a baseline level. In some embodiments, the baseline duration may be about 1 second to about 5 seconds. In various embodiments, the baseline duration may be about 1 second, about 2 seconds, about 3 seconds, about 4 seconds, about 5 seconds, about 10 seconds, about 20 seconds, about 30 seconds, about 1 minute, and any value or range between any two of these values (including endpoints). In some embodiments, resistance at the pressurized pressure and low frequency ($R_P$, 5) and resistance at the pressurized pressure and high frequency ($R_P$, 1000) may represent resistance in the interstitial volume ($R_P$, E) and in the tissue including ECV+ICV ($R_P$, T) excluding blood volume in calf 510. Referring to FIG. 6, therein is depicted a graph 605 illustrating a wave of change in extracellular resistance as the cBIS analysis changes from baseline cBIS ($R_0$) to pressurized cBIS ($R_P$).

Figure 7:
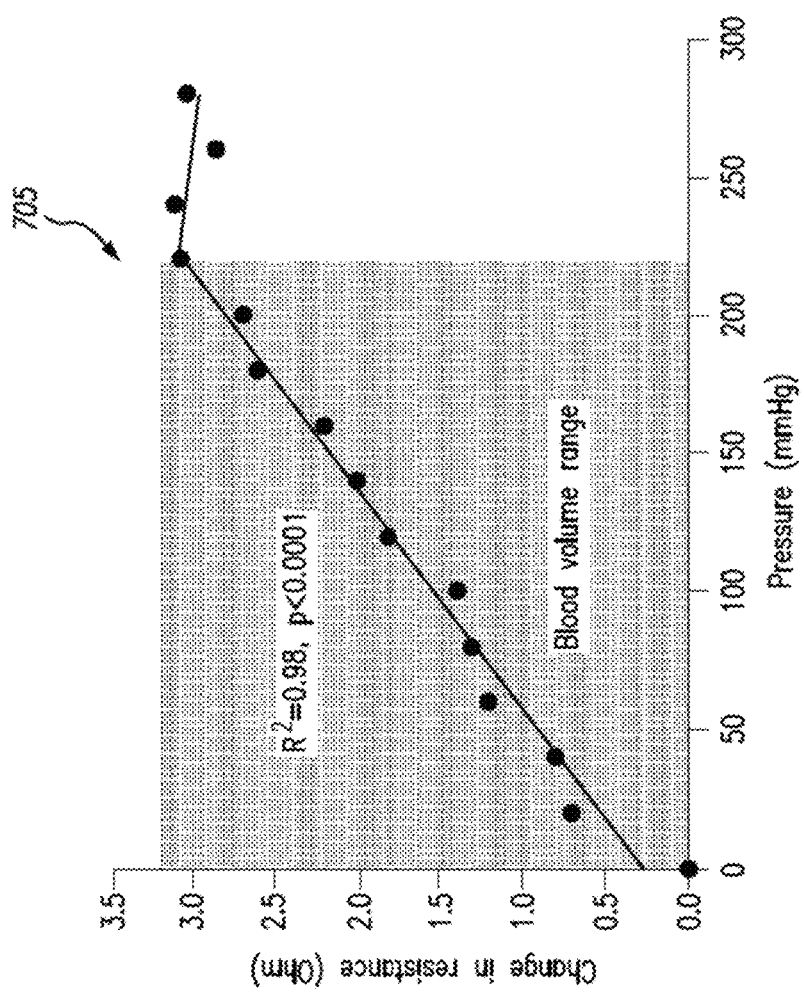
FIG. 7 illustrates a graph depicting an exemplary relationship between change in resistance and change in pressure applied by a blood pressure device.

FIG. 7 depicts a graph 705 illustrating a relationship between change in resistance (for example, representing a change in fluid volume) and change in pressure applied by a blood pressure device (for example, cuff 525). Graph 705 illustrates change in resistance recorded by a bioimpedance device as pressure is increased step-by-step by a blood pressure device. As indicated by graph 705, an increase in resistance may represent a decrease in fluid volume when the pressure was increased up to 220 mmHg. However, above this pressure (>220 mmHg), resistance does not increase further. Accordingly, all or substantially all of the blood volume has been squeezed out from the area so that interstitial fluid volume may be determined using the extracellular resistance according to some embodiments.

A relationship between tissue volume and resistance may be described according to the following Equation (1):

$$\text{Volume} = \rho_j \frac{L^2}{R_j},$$

Where $\rho_j$ and $R_j$ represent resistivity and resistance in a specific fluid compartment, for example, j=E in ECV or j=T in TBW. ECV consists of plasma (PV) and interstitial volume according to the following Equation (2):

$$ECV = PV + V_{IT}.$$

According to Equation (1), Equation (2) may be expressed as the following Equation (3):

$$\frac{1}{R_{0,E}} = \frac{1}{R_{PV}} + \frac{1}{R_{P,E}},$$

where $R_{PV}$ represents resistance in plasma which is unknown in Equation (3). However, the ration of PV to $V_{IT}$ can be determined based on the following Equations (4) and (5):

$$\frac{PV}{V_{IT}} = \frac{\rho_E \frac{L^2}{R_{PV}}}{\rho_E \frac{L^2}{R_{P,E}}} = \frac{R_{P,E}}{R_{PV}} = \frac{R_{P,E}}{R_{0,E}} - 1,$$

$$PV = V_{IT}\left(\frac{R_{P,E}}{R_{0,E}} - 1\right).$$

In some embodiments, Equation (5) may represent total body ECV. Accordingly, applying Equation (5) to Equation (2) may provide total body $V_{IT}$ according to the following Equation (6):

$$V_{IT} = ECV\left(\frac{R_{0,E}}{R_{P,E}}\right)$$

In various embodiments, when $R_{0,E}$ and $R_{P,E}$ are replaced by $R_{0,T}$ and $R_{P,T}$ using 1000 kHz resistance, the relationship of $BV_P$ and TBW may be determined according to the following Equation (7):

$$BV_P = TBW\left(1 - \frac{R_{0,T}}{R_{P,T}}\right).$$

In some embodiments, according to Equation (7), $BV_P$ may be calculated with a known TBW and the ratio of baseline resistance to resistance with increased (or pressurized) pressure. In various embodiments, the resistance ratio of a portion of the human body, such as a calf, may represent total body, so that total body $BV_P$ (or BV) may be determined with whole body TBW.

Accordingly, in some embodiments, $V_{IT}$ and $BV_P$ may be determined by using a multi-frequency bioimpedance technique in combination with a blood pressure device. In various embodiments, measurement of BIS may provide multi-frequency resistances which reflect ECV and TBW at baseline measurement without blood pressure device pressure in a body segment. With inflation of blood pressure device pressure, a plurality of resistances, such as two resistances, that may reflect $V_{IT}$, ECV, and ICV, without blood in the vessel, can be assessed separately in the body segment with low and high frequency resistances, respectively. In exemplary embodiments, it is assumed that the ratios of resistances are the same or substantially the same as in the whole body so that whole body $V_{IT}$ and $BV_P$ may be estimated or otherwise determined.

Methods according to some embodiments can be applied in clinical studies without requiring radiation doses and equilibrium time. Measurement of bioimpedance is a non-invasive technique and blood pressure cuff pressure increases with regular SBP measurement can be made in a short time frame, such as in the range of a few seconds. Peripheral plasma, whole blood and interstitial volume measurements are helpful to understand relationships between normal fluid status and change in blood volume, for example, in dialysis (for instance, HD) patients.

Figure 10:
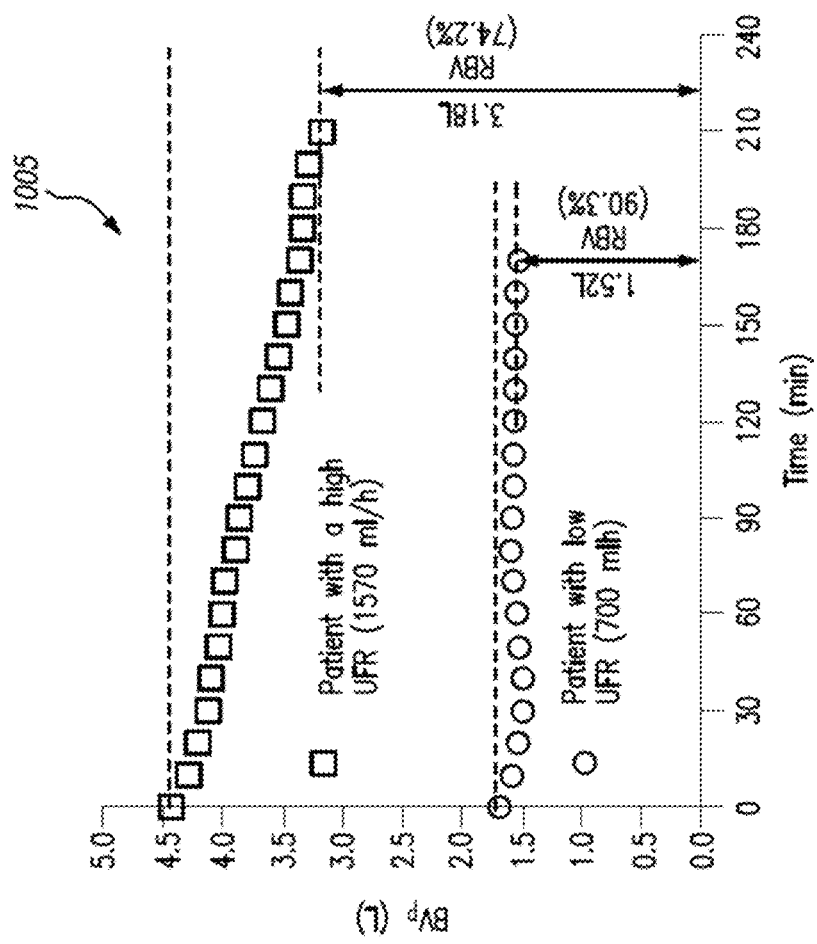
FIG. 10 illustrates a graph depicting an exemplary change in peripheral blood volume ($BV_P$) as compared to change in relative blood volume (RBV).

Intradialytic change in $BV_P$ and interstitial fluid volume may provide useful references to set parameters for performing dialysis, such as UFR and UFV in order to reduce negative symptoms, for example intradialytic hypotension (IDH) during HD treatment. $BV_P$ may be estimated or otherwise determined according to some embodiments at the beginning of HD, and can be calculated during the treatment according to change in RBV (%). FIG. 10 shows an example of how $BV_P$, rather than RBV, may impart an important role in the understanding of individual hemodynamic responses during UF and HD. In addition, RBV monitoring can be very useful to calculate $BV_P$ over the entire treatment when the initial blood volume is available. Moreover, if a monitor of $BV_P$ is integrated into an HD machine, change in interstitial fluid and blood volume can be measured continuously, which may, among other things, facilitate preventing or mitigating IDH in clinical practice. Accordingly, some embodiments may provide processes to continuously monitor $V_{IT}$ and/or $BV_P$ including plasma and whole blood volume in a dialysis device, such as an HD device for dialysis patients. For example, in some embodiments, a dialysis device or other computing device may include a display of $V_{IT}$ and/or $BV_P$ monitored according to some embodiments during a procedure. In other embodiments, a dialysis device or other computing device may provide alarms, alerts, or other messages based on $V_{IT}$ and/or $BV_P$ monitored according to some embodiments during a procedure, for instance, if $V_{IT}$ and/or $BV_P$ monitored are outside of a respective threshold value. Moreover, with such efficient, low-cost and noninvasive methods, monitoring changes in peripheral blood volume could be performed with a RBV monitor.

Accordingly, some embodiments provide an efficient and noninvasive technique to assess $V_{IT}$ and/or $BV_P$ in hemodialysis patients using bioimpedance measurements. Techniques according to some embodiments could be applied, for example, to monitor intradialytic change in absolute blood volume and interstitial fluid volume in the non-central BV compartment. In addition, an understanding of the relationship between change in interstitial fluid and blood volumes may protect against or mitigate IDH by adjusting UFR during HD. In addition, knowledge of this relationship may improve mathematic modeling of dynamic fluid shifts between body fluid compartments during hemodialysis. Embodiments are not limited in this context.

Figure 8:
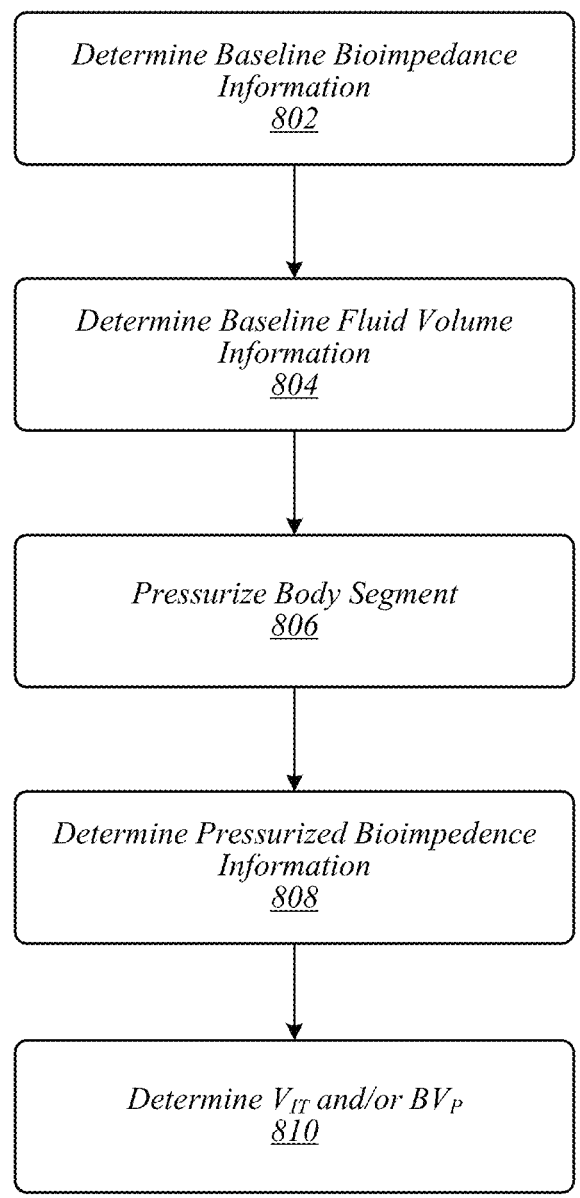
FIG. 8 illustrates an embodiment of a logic flow.

FIG. 8 illustrates an embodiment of a logic flow 800. Logic flow 800 may be representative of some or all of the operations executed by one or more embodiments described herein, such as apparatus 105, healthcare information exchange platform 205, and/or integrated care system 305 and/or 405. Although logic flow 800 is represented in FIG. 8 as occurring in a particular order, embodiments are not so limited, as blocks may be performed out of order, simultaneously, or not performed. In some embodiments, logic flow 800 may be representative of some or all of the operations of a fluid volume analysis process.

At block 802, logic flow 800 may determine baseline bioimpedance information. For example, a whole body bioimpedance system and/or bioimpedance system 505 may determine baseline bioimpedance information under normal or non-pressurized conditions. In some embodiments, logic flow 800 may perform BIS (for instance, wBIS and/or cBIS) at different current frequencies, such as a low frequency (for instance, about 5 kHz) and a high frequency (for example 1000 kHz).

Logic flow 800 may determine baseline fluid volume information at block 804. For example, fluid volume application 132 may receive the baseline bioimpedance information from bioimpedance device 150b (for example, implemented as bioimpedance system 505) and may determine ECV and/or TBW. At block 806, logic flow 800 may pressurize a body segment of the patient. For example, in some embodiments, logic flow 800 may control a blood pressure device 150a (for example, cuff 525) to a certain pressure (for instance, SBP). In other embodiments, logic flow 800 may provide a signal for an operator to control a blood pressure device 150a, receive an indication that a blood pressure device 150a has been activated, and/or the like.

At block 808, logic flow 800 may determine pressurized bioimpedance information. For example, pressurized cBIS may be initiated as cBIS is continuously measured as cuff 525 is inflated to a pressurized pressure. At block 810, logic flow 800 may determine $V_{IT}$ and/or $BV_P$. For example, fluid volume application 132 may process the pressurized bioimpedance information according to one or more of Equations (1)-(7) to determine $V_{IT}$ and/or $BV_P$.

Experiment

Bioimpedance Study of Dialysis Patients

Thirty-five HD patients were studied pre- and post-HD. ECB and TBW were measured using wBIS and cBIS. The calf resistances at 5 kHz (R5) and at 1000 kHz (R1000), respectively reflect ECV and TBW in the calf. A blood pressure cuff was placed over the area of cBIS. Regional and whole body plasma or $BV_P$ and $V_{IT}$ or total fluid volume are measured at R5 or R1000 when the cuff was inflated to just above the SBP. According to calf normalized resistivity (CNR) post-HD, patients were divided into two groups: overhydration (OH, CNR<18.5, $10-2*\Omega m3/kg$) and normal hydration (NH, CNR≥18.5, $10-2*\Omega m3/kg$). $BV_P$ was higher in OH than in NH group which can be explained by the low ratio of change in $V_{IT}$ to ultrafiltration volume in the OH group (0.57±0.23 vs 0.83±0.45 L, p<0.05).

A Hydra 4200 bioimpedance device manufactures by Xitron Technologies Inc. of San Diego, Calif. was used. Four electrodes were placed on the calf. An automatic blood pressure monitor was used with a blood pressure cuff over the area of the measuring calf to displace blood volume when the pressure exceeded SBP. A whole body bioimpedance measurement was performed with the same bioimpedance device. Two electrodes were placed on one hand and foot to inject current and two electrodes were placed on the wrist and ankle to measure voltage to provide ECV and TBW in the body. A relative blood volume (RBV) monitor provided change in the water content of blood during HD based on the initial value of measurement. RBV was recorded every 10 minutes. Calf ECV and TBW were measured and calf normalized resistivity (CNR) was calculated to determine the hydration status of patients. Ultrafiltration volumes (UFV) and rates (UFR) were recorded.

The mean of baseline measurement for 30 seconds was used to represent the resistance without squeezing blood volume. The data were presented as means and SD. P value<0.05 was considered to be a significant difference in means between the two groups. Data in 35 patients in whom calf and whole body bioimpedance had been successfully measured are shown in Table 1 as a summary of pre-HD information. Table I shows that there was no difference in body weight (Wt), ECV, TBW, change in RBV and UFV or UFR between the two groups with different hydration status.

TABLE 1

|  | OH (n = 22) | NH (n = 13) | P value |
|---|---|---|---|
| Gender | F = 12 | F = 5 | ns |
| Age (Year) | 55.5 ± 11 | 54.8 ± 10 | ns |
| Pre-HD Wt (kg) | 78.1 ± 19 | 79.5 ± 17 | ns |
| Post-HD Wt (kg) | 75.1 ± 19 | 76.7 ± 16 | ns |
| UFV (L) | 3.5 ± 1.2 | 3.2 ± 1.2 | ns |
| UFR (ml/h) | 1037 ± 287 | 918 ± 330 | ns |
| RBV at end HD | 87.1 ± 5.9 | 84.8 ± 6.4 | ns |
| Pre-HD ECV (L) | 18.1 ± 4.4 | 18.3 ± 4 | ns |
| Pre-HD TBW (L) | 39.3 ± 9.9 | 38.5 ± 8.5 | ns |

Table 2 shows that all resistances differed significantly between the two groups. Slight but insignificant (p=0.07) difference in PV pre-HD. $BV_P$ was significantly higher in OH than in the NH group pre-HD but no difference in post-HD $BV_P$ calculated with Equation (7) was observed between the groups. However, $BV_P$ at the end HD calculated using RBV was significantly lower in NH than in the OH groups. The values of plasma and interstitial volume were not different between two groups.

TABLE 2

|  | OH (n = 22) | NH (n = 13) | P value |
|---|---|---|---|
| Pre $R_{0, E}$ (Ω) | 40.9 ± 6.8 | 49.5 ± 7.3 | <0.01 |
| Pre $R_{P, E}$ (Ω) | 44.4 ± 7.5 | 52.9 ± 8.2 | <0.01 |
| Pre $R_{0, T}$ (Ω) | 26.2 ± 4.6 | 31.6 ± 5.6 | <0.01 |
| Pre $R_{P, T}$ (Ω) | 29.0 ± 5 | 34.2 ± 6.2 | <0.05 |
| Post $R_{0, E}$ (Ω) | 50.4 ± 7.8 | 63.4 ± 8.9 | <0.0001 |
| Post $R_{P, E}$ (Ω) | 54.4 ± 8.4 | 67.7 ± 10.1 | <0.0001 |
| Post $R_{0, T}$ (Ω) | 30.2 ± 5.7 | 38.8 ± 10.6 | <0.01 |
| Post $R_{P, T}$ (Ω) | 33.2 ± 6.1 | 41.8 ± 10.5 | <0.01 |
| Pre $V_{IT}$ (L) | 16.6 ± 4.1 | 17.2 ± 3.9 | ns |
| Pre PV (L) | 1.4 ± 0.6 | 1.1 ± 0.3 | 0.07 |
| Pre $BV_P$ (L) | 3.9 ± 1.6 | 2.8 ± 0.7 | <0.05 |
| Post $V_{IT}$ (L) | 14.7 ± 3.6 | 14.9 ± 3.3 | ns |
| Post PV (L) | 1.2 ± 0.5 | 0.96 ± 0.4 | ns |
| Post $BV_P$ (L) | 3.5 ± 1.5 | 2.9 ± 1.2 | ns |
| Δ $V_{IT}$/UFV (L) | 0.57 ± 0.23 | 0.83 ± 0.45 | <0.05 |
| $BV_P$ at end of HD# (L) | 3.56 ± 1.4 | 2.6 ± 0.58 | <0.05 |

In Table 2, Δ $V_{IT}$ represents a change in $V_{IT}$ between pre- and post-HD and $BV_P$ at end of HD# is determined with pre-HD $BV_P$ times RBV (%) at the end of treatment.

Figure 9:
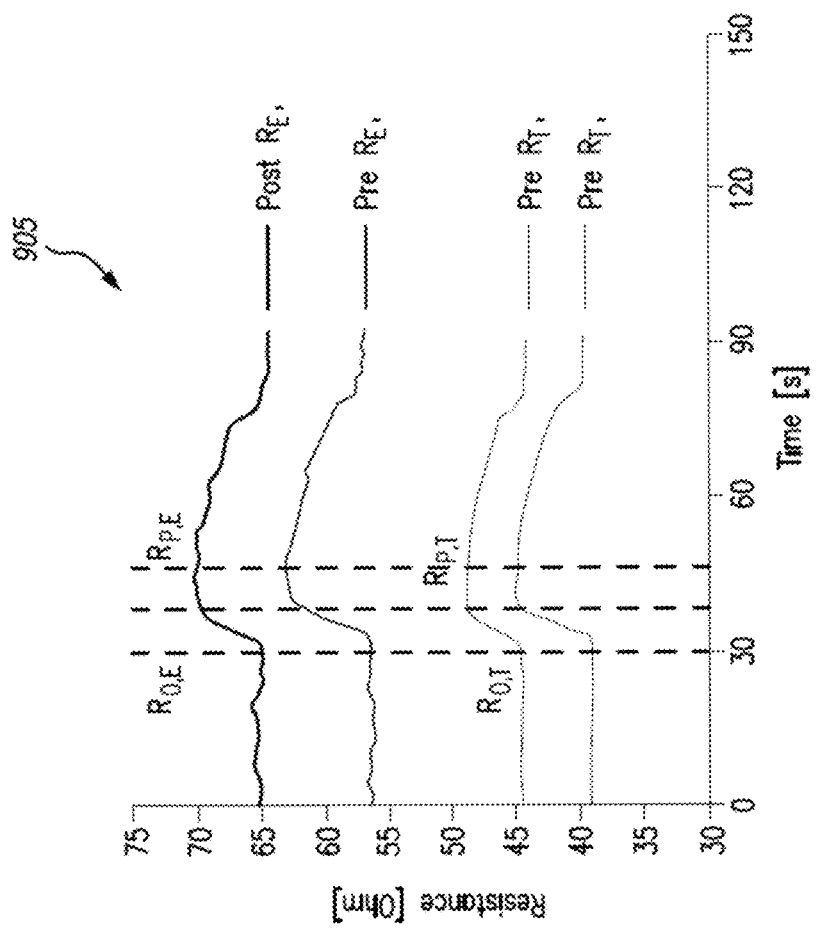
FIG. 9 illustrates a graph depicting an exemplary change in resistance based on a change in pressure applied by a blood pressure device.

FIG. 9 illustrates a graph 905 depicting the change in resistances in a typical patient. Resistance increased from baseline, ($R_0$, time from 0 to 30 seconds) to the maximum point ($R_P$, time at 38 and 46 seconds at $R_P$, T and $R_P$, E respectively) due to squeezing blood volume from this area by increasing cuff pressures. Resistances $R_0$ and $R_P$ were higher post-HD than pre-HD because of the removal of fluid. Values of $R_T$ were less than $R_E$ both pre- and post-HD because $R_T$ represents both ECV and ICV.

Intradialytic change in blood volume can be calculated using $BV_P$ at the beginning of HD and multiplying change in RBV (%). FIG. 10 illustrates a graph 1005 depicting change in $BV_P$ (L) in two cases compared to change in RBV (%). Changes in $BV_P$ are shown at 10-minute intervals. In the first case, a small change in RBV, such as a less than 10% change in RBV (FIG. 10 (o)) represents $BV_P$ of 1.52 L. In the second case (FIG. 10 (□)) change was in more than 25% of RBV representing $BV_P$ of 3.18 L.

For example, although body weight, ECV, TBW, RBV and UFV did not differ significantly between two groups at baseline, the OH group remained fluid overloaded at the end of treatment (post-HD CNR=14.4±2, 10−2 Ωm3/kg) compared to NH (post-HD CNR=20.4±2, 10−2 Ωm3/kg). One explanation could be that ultrafiltration efficiency defined as Δ$V_{IT}$/UFV was significantly lower (p<0.05) in the OH (0.57±0.23) than in the NH (0.83±0.45) groups (see, for example, Table 2).

Figure 11:
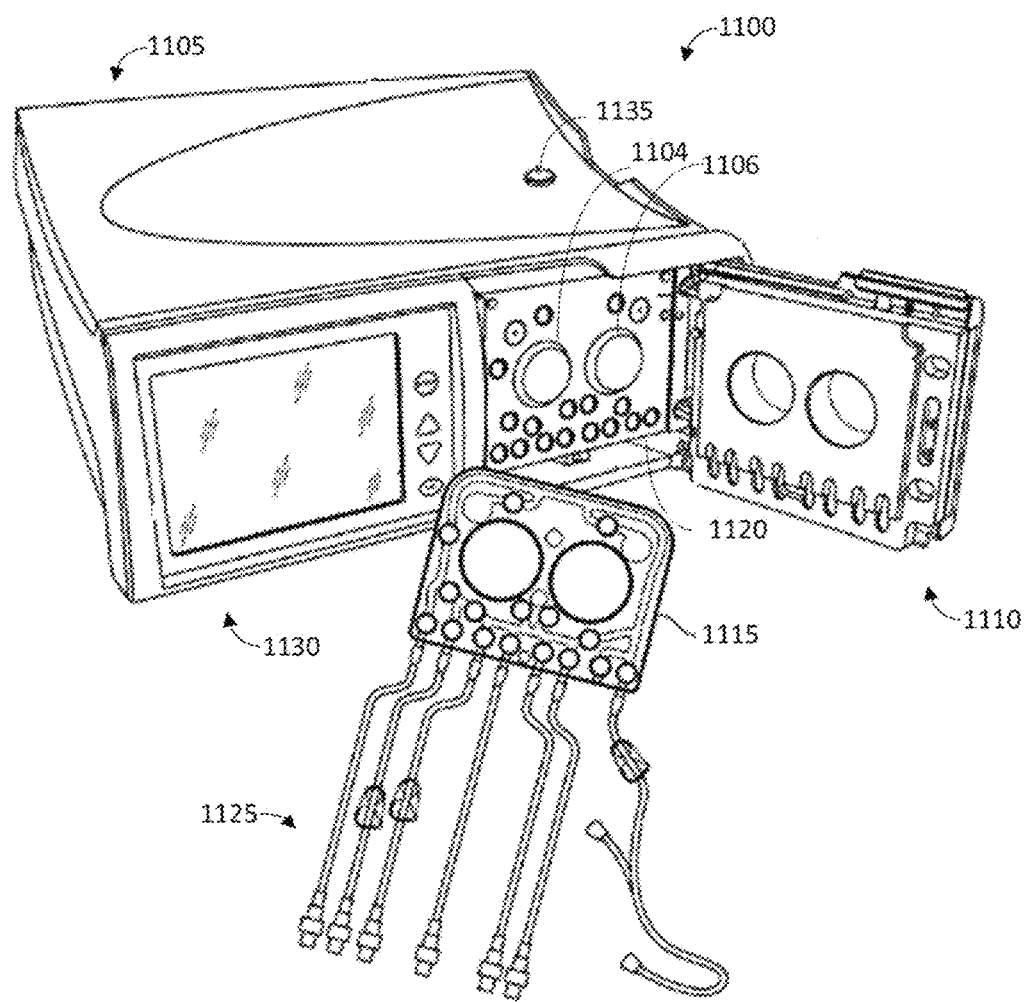
FIG. 11 illustrates an example peritoneal dialysis device.

Referring now to FIG. 11, a dialysis machine 1100 according to an embodiment of the present disclosure is shown. The machine 1100 may include a housing 1105, a door 1110 for receiving a cartridge 1115 in a cavity 1120, and a user interface portion 1130. Fluid lines 1125 may be coupled to the cartridge in a known manner, such as via a connector, and may further include valves for controlling fluid flow to and from fluid bags including fresh dialysate and warming fluid. In another embodiment, at least a portion of fluid lines 1125 may be integral to cartridge 1115. Prior to operation, a user may open door 1110 to insert a new cartridge 1115 and/or to remove a used cartridge 1115 after operation.

Cartridge 1115 may be placed in cavity 1120 of machine 1100 for operation. During operation, dialysate fluid may be flowed into a patient's abdomen via cartridge 1115, and spent dialysate, waste, and/or excess fluid may be removed from the patient's abdomen via cartridge 1115. Door 1110 may be securely closed to machine 1100. Peritoneal dialysis for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

User interface portion 1130 may be a touch screen, and may include one or more buttons for selecting and/or entering user information. User interface portion 1130 may be operatively connected to a controller (not shown) and disposed in machine 1100 for receiving and processing the inputs to operate dialysis machine 1100. In some embodiments, fluid volume information determined according to some embodiments may be displayed via user interface portion 1130.

In some embodiments, machine 1100 may wirelessly transmit (for example, via a wireless connection), alternatively or simultaneously or in coordination with sending information to computing device 110, healthcare exchange platform 205, and/or integrated care system 305 and/or 405, information or alerts to a remote location, including but not limited to a doctor's office, hospital, call center, and technical support. For example, machine 1100 may provide real time remote monitoring of machine operation and patient parameters, including fluid volume information ($V_{IT}$ and/or $BV_P$) determined according to some embodiments. Machine 1100 may include a memory, such as memory 130, to store data and/or machine 1100 may transmit data to a local or remote server at scheduled intervals. For example, machine 1100 may send patient data to computing device 110, healthcare exchange platform 205, and/or integrated care system 305 and/or 405, for use in the one or more algorithms, processes, and/or the like as data for performing a fluid volume analysis according to some embodiments. In some embodiments, machine 1100 may be operably coupled to a blood pressure device and/or a bioimpedance device to facilitate a fluid volume analysis according to some embodiments.

Figure 12:
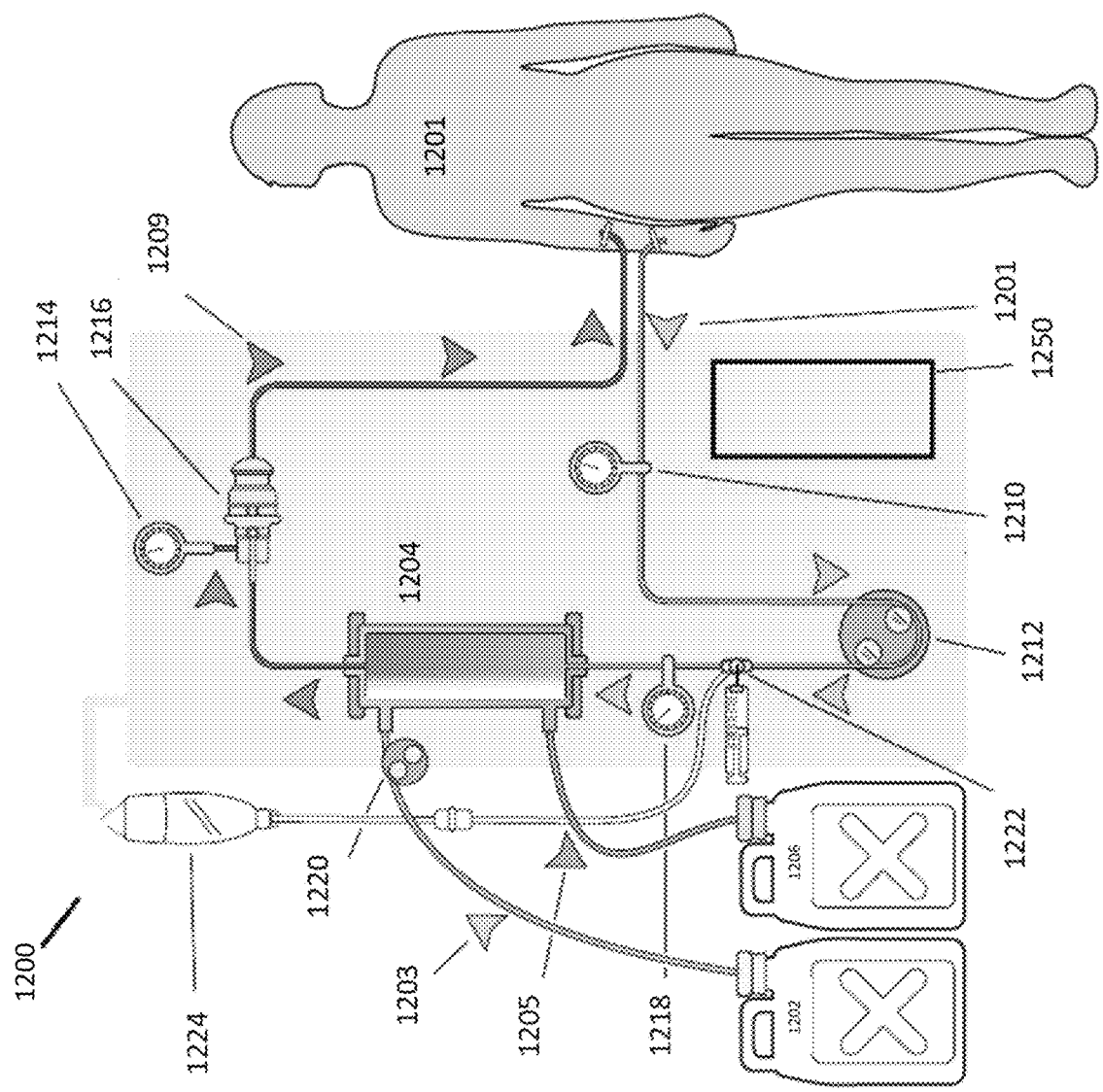
FIG. 12 illustrates an example hemodialysis system.

FIG. 12 illustrates a diagram of an exemplary embodiment of a dialysis system 1200 in accordance with the present disclosure. Dialysis system 1200 may be configured to provide hemodialysis (HD) treatment for a patient 1201. Fluid reservoir 1202 may deliver fresh dialysate to a dialyzer 1204 via tubing 1203, and reservoir 1206 may receive spent dialysate once it has passed through dialyzer 1204 via tubing 1205. A hemodialysis operation may filter particulates and/or contaminates from a patient's blood through a patient external filtration device, for example, a dialyzer 1204. As the dialysate is passed through dialyzer 1204, unfiltered patient blood is also passed into dialyzer 1204 via tubing 1207 and filtered blood is returned to patient 1201 via tubing 1209. Arterial pressure may be monitored via pressure sensor 1210, inflow pressure monitored via sensor 1218, and venous pressure monitored via pressure sensor 1214. An air trap and detector 1216 may ensure that air is not introduced into patient blood as it is filtered and returned to patient 1201. The flow of blood and the flow of dialysate may be controlled via respective pumps, including a blood pump 1212 and a fluid pump 1220. Heparin 1222, a blood thinner, may be used in conjunction with saline 1224 to ensure blood clots do not form or occlude blood flow through the system.

In some embodiments, dialysis system 1200 may include a controller 1250, which may be similar to computing device 110 and/or components thereof (for instance, processor circuitry 120). Controller 1250 may be configured to monitor fluid pressure readings to identify fluctuations indicative of patient parameters, such as heart rate and/or respiration rate. In some embodiments, a patient heart rate and/or respiration rate may be determinable by the fluid pressure in the fluid flow lines and fluid bags. In various embodiments, controller may receive and/or calculate fluid volume information (such as $V_{IT}$ and/or $BV_P$). Controller 1250 may also be operatively connected to and/or communicate with additional sensors or sensor systems, devices, and/or the like, although controller 1250 may use any of the data available on the patient's biologic functions or other patient parameters. For example, controller 1250 may send patient data to computing device 110, healthcare exchange platform 205, and/or integrated care system 305 and/or 405 to determine fluid volumes according to some embodiments. Machine 1200 and/or components thereof, such as controller 1250, may be operably coupled to a blood pressure device and/or a bioimpedance device to determine fluid volume information and/or to provide data to facilitate the determination of fluid volume information (for instance, $V_{IT}$ and/or $BV_P$) by computing device 110, healthcare exchange platform 205, and/or integrated care system 305 and/or 405.

FIG. 13 illustrates an embodiment of an exemplary computing architecture 1300 suitable for implementing various embodiments as previously described. In various embodiments, the computing architecture 1300 may comprise or be implemented as part of an electronic device. In some embodiments, the computing architecture 1300 may be representative, for example, of computing device 110 and/or components of healthcare exchange platform 205 and/or integrated care system 305 and/or 405. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 1300. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1300 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1300.

As shown in FIG. 13, the computing architecture 1300 comprises a processing unit 1304, a system memory 1306 and a system bus 13013. The processing unit 1304 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1304.

The system bus 13013 provides an interface for system components including, but not limited to, the system memory 1306 to the processing unit 1304. The system bus 13013 can be any of several types of bus structure that may further interconnect to a memory bus (with or without a memory controller), a peripheral bus, and a local bus using any of a variety of commercially available bus architectures. Interface adapters may connect to the system bus 13013 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1306 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 13, the system memory 1306 can include non-volatile memory 1310 and/or volatile memory 1312. A basic input/output system (BIOS) can be stored in the non-volatile memory 1310.

The computer 1302 may include various types of computer-readable storage media in the form of one or more lower speed memory units, including an internal (or external) hard disk drive (HDD) 1314, a magnetic floppy disk drive (FDD) 1316 to read from or write to a removable magnetic disk 13113, and an optical disk drive 1320 to read from or write to a removable optical disk 1322 (e.g., a CD-ROM or DVD). The HDD 1314, FDD 1316 and optical disk drive 1320 can be connected to the system bus 13013 by a HDD interface 1324, an FDD interface 1326 and an optical drive interface 13213, respectively. The HDD interface 1324 for external drive implementations can include at least one or both of Universal Serial Bus (USB) and IEEE 13134 interface technologies.

The drives and associated computer-readable media provide volatile and/or nonvolatile storage of data, data structures, computer-executable instructions, and so forth. For example, a number of program modules can be stored in the drives and memory units 1310, 1312, including an operating system 1330, one or more application programs 1332, other program modules 1334, and program data 1336. In one embodiment, the one or more application programs 1332, other program modules 1334, and program data 1336 can include, for example, the various applications and/or components of apparatus 105, 205, 305, and/or 405.

A user can enter commands and information into the computer 1302 through one or more wire/wireless input devices, for example, a keyboard 13313 and a pointing device, such as a mouse 1340. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1304 through an input device interface 1342 that is coupled to the system bus 13013, but can be connected by other interfaces such as a parallel port, IEEE 1394 serial port, a game port, a USB port, an IR interface, and so forth.

A monitor 1344 or other type of display device is also connected to the system bus 13013 via an interface, such as a video adaptor 1346. The monitor 1344 may be internal or external to the computer 802. In addition to the monitor 1344, a computer typically includes other peripheral output devices, such as speakers, printers, and so forth.

The computer 1302 may operate in a networked environment using logical connections via wire and/or wireless communications to one or more remote computers, such as a remote computer 13413. The remote computer 13413 can be a workstation, a server computer, a router, a personal computer, portable computer, microprocessor-based entertainment appliance, a peer device or other common network node, and typically includes many or all of the elements described relative to the computer 1302, although, for purposes of brevity, only a memory/storage device 1350 is illustrated. The logical connections depicted include wire/wireless connectivity to a local area network (LAN) 1352 and/or larger networks, for example, a wide area network (WAN) 1354. Such LAN and WAN networking environments are commonplace in offices and companies, and facilitate enterprise-wide computer networks, such as intranets, all of which may connect to a global communications network, for example, the Internet.

When used in a LAN networking environment, the computer 1302 is connected to the LAN 1352 through a wire and/or wireless communication network interface or adaptor 1356. The adaptor 1356 can facilitate wire and/or wireless communications to the LAN 1352, which may also include a wireless access point disposed thereon for communicating with the wireless functionality of the adaptor 1356.

When used in a WAN networking environment, the computer 1302 can include a modem 13513, or is connected to a communications server on the WAN 1354, or has other means for establishing communications over the WAN 1354, such as by way of the Internet. The modem 13513, which can be internal or external and a wire and/or wireless device, connects to the system bus 13013 via the input device interface 1342. In a networked environment, program modules depicted relative to the computer 1302, or portions thereof, can be stored in the remote memory/storage device 1350. It will be appreciated that the network connections shown are exemplary and other means of establishing a communications link between the computers can be used.

The computer 1302 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus, comprising:
   at least one memory; and
   logic coupled to the at least one memory, the logic to:
      receive baseline bioimpedance information for at least a portion of a human body of a patient at a baseline pressure during a dialysis treatment of the patient performed by a dialysis system,
      receive pressurized bioimpedance information of the portion of the human body at a pressurized pressure, the pressurized pressure greater than the baseline pressure and configured to substantially remove blood volume from the portion at the pressurized pressure, the baseline bioimpedance information and the pressurized bioimpedance information generated at one of a low current frequency and a high current frequency,
      determine at least one of:
         interstitial fluid volume ($V_{IT}$) based on the baseline bioimpedance information and the pressurized bioimpedance information generated at the low current frequency, or
         peripheral blood volume ($BV_p$) based on the baseline bioimpedance information and the pressurized bioimpedance information generated at the high current frequency, and
      control the administration of the dialysis treatment to the patient via setting one of an ultrafiltration rate (UFR) or an ultrafiltration volume (UFV) based on at least one of $V_{IT}$ or $BV_p$.

2. The apparatus of claim 1, the baseline bioimpedance information generated via at least one of whole body bioimpedance spectroscopy (wBIS) or calf bioimpedance spectroscopy (cBIS).

3. The apparatus of claim 1, the baseline pressure is about 0 mmHg.

4. The apparatus of claim 1, the pressurized pressure is about a systolic blood pressure (SBP).

5. The apparatus of claim 1, the logic to:
   determine extracellular volume (ECV) based on the baseline bioimpedance information, and
   determine $V_{IT}$ based on ECV and the pressurized bioimpedance information.

6. The apparatus of claim 1, the logic to:
   determine total body water (TBW) based on the baseline bioimpedance information, and
   determine $BV_p$ based on TBW and the pressurized bioimpedance information.

7. The apparatus of claim 1, the pressurized bioimpedance information generated by performing calf bioimpedance spectroscopy (cBIS) on a calf of the human body pressurized by a blood pressure cuff.

8. The apparatus of claim 5, the logic to determine $V_{IT}$ according to the following:

$$V_{IT} = ECV\left(\frac{R_{0,E}}{R_{P,E}}\right),$$

where $R_{0,E}$ is a first resistance value at the baseline pressure and the low current frequency and $R_{P,E}$ is a second resistance value at the pressurized pressure and the low current frequency.

9. The apparatus of claim 6, the logic to determine $BV_p$ according to the following:

$$BV_P = TBW\left(1 - \frac{R_{0,T}}{R_{P,T}}\right),$$

where $R_{0,T}$ is a first resistance value at the baseline pressure and the high current frequency and $R_{P,T}$ is a second resistance value at the pressurized pressure and the high current frequency.

10. A method, comprising:
    determining baseline bioimpedance information for at least a portion of a human body of a patient at a baseline pressure during a dialysis treatment of the patient performed by a dialysis system;
    determining pressurized bioimpedance information of the portion of the human body at a pressurized pressure, the pressurized pressure greater than the baseline pressure and configured to substantially remove blood volume from the portion at the pressurized pressure, the baseline bioimpedance information and the pressurized bioimpedance information generated at one of a low current frequency and a high current frequency;
    determining at least one of:
       interstitial fluid volume ($V_{IT}$) based on the baseline bioimpedance information and the pressurized bioimpedance information generated at the low current frequency, or
       peripheral blood volume ($BV_P$) based on the baseline bioimpedance information and the pressurized bioimpedance information generated at the high current frequency, and
    controlling the administration of the dialysis treatment to the patient via setting one of an ultrafiltration rate (UFR) or an ultrafiltration volume (UFV) based on at least one of $V_{IT}$ or $BV_P$.

11. The method of claim 10, the baseline bioimpedance information generated via at least one of whole body bioimpedance spectroscopy (wBIS) or calf bioimpedance spectroscopy (cBIS).

12. The method of claim 10, the baseline pressure is about 0 mmHg.

13. The method of claim 10, the pressurized pressure is about a systolic blood pressure (SBP).

14. The method of claim 10, comprising:
determining extracellular volume (ECV) based on the baseline bioimpedance information, and
determining $V_{IT}$ based on ECV and the pressurized bioimpedance information.

15. The method of claim 10, comprising:
determining total body water (TBW) based on the baseline bioimpedance information, and
determining $BV_P$ based on TBW and the pressurized bioimpedance information.

16. The method of claim 10, the pressurized bioimpedance information generated by performing calf bioimpedance spectroscopy (cBIS) on a calf of the human body pressurized by a blood pressure cuff.

17. The method of claim 14, comprising determining $V_{IT}$ according to the following:

$$V_{IT} = ECV\left(\frac{R_{0,E}}{R_{P,E}}\right),$$

where $R_{0,E}$ is a first resistance value at the baseline pressure and the low current frequency and $R_{P,E}$ is a second resistance value at the pressurized pressure and the low current frequency.

18. The method of claim 15, comprising determining $BV_P$ according to the following:

$$BV_P = TBW\left(1 - \frac{R_{0,T}}{R_{P,T}}\right),$$

where $R_{0,T}$ is a first resistance value at the baseline pressure and the high current frequency and $R_{P,T}$ is a second resistance value at the pressurized pressure and the high current frequency.

19. The apparatus of claim 1, wherein the low current frequency is about 5 kHz and the high current frequency is about 1000 kHz.

20. The method of claim 10, wherein the low current frequency is about 5 kHz and the high current frequency is about 1000 kHz.

* * * * *